United States Patent
Cai et al.

(10) Patent No.: US 9,597,433 B2
(45) Date of Patent: Mar. 21, 2017

(54) NON-PATHOGENIC BIOFILMS AND USES THEREOF

(71) Applicants: Chengzhi Cai, Pearland, TX (US); Fei Yu, Houston, TX (US); Analette Lopez, Missouri City, TX (US)

(72) Inventors: Chengzhi Cai, Pearland, TX (US); Fei Yu, Houston, TX (US); Analette Lopez, Missouri City, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 177 days.

(21) Appl. No.: 14/466,325

(22) Filed: Aug. 22, 2014

(65) Prior Publication Data

US 2015/0057641 A1    Feb. 26, 2015

Related U.S. Application Data

(60) Provisional application No. 61/869,349, filed on Aug. 23, 2013.

(51) Int. Cl.
*A61L 29/08*    (2006.01)
*A61L 29/16*    (2006.01)

(52) U.S. Cl.
CPC ............. *A61L 29/085* (2013.01); *A61L 29/16* (2013.01); *A61L 2400/18* (2013.01); *Y10T 428/31663* (2015.04)

(58) Field of Classification Search
CPC .................................................... A61L 29/085
See application file for complete search history.

(56) References Cited

U.S. PATENT DOCUMENTS

| | | | |
|---|---|---|---|
| 6,719,991 B2 | 4/2004 | Darouiche et al. | |
| 7,790,183 B2 | 9/2010 | Darouiche et al. | |
| 8,802,078 B2 * | 8/2014 | Cai ........................... | 424/93.45 |
| 2009/0041727 A1 | 2/2009 | Suzuki et al. | |
| 2011/0020307 A1 | 1/2011 | Suzuki et al. | |
| 2011/0150880 A1 | 6/2011 | Pier et al. | |
| 2012/0230957 A1 | 9/2012 | Rudick et al. | |
| 2012/0231518 A1 | 9/2012 | Cai | |
| 2012/0309701 A1 | 12/2012 | Janetka et al. | |

FOREIGN PATENT DOCUMENTS

WO    WO-9832790 A1    7/1998

OTHER PUBLICATIONS

Brooks, T., et al, "A simple artificial urine for the growth of urinary pathogens," Letters in Applied Microbiology, 1997, 24, pp. 203-206.
Bergsten G, Wullt B, Schembri MA, Leijonhufvud I, Svanborg C. Do type 1 fimbriae promote inflammation in the human urinary tract? *Cellular Microbiology* 2007, 9, 1766-1781.
Cha BJ, Kang YS, Won J. Preparation and characterization of dendrimer layers on poly(dimethylsiloxane) films. *Macromolecules* 2001,34, 6631-6636.
Darouiche RO, Riosa S, Hull RA. Comparison of *Escherichia coli* Strains as Agents for Bacterial Interference. *Infection Control and Hospital Epidemiology 2010*, 31, 659-661.
Trautner BW, et al. Increased expression of type-1 fimbriae by nonpathogenic *Escherichia coli* 83972 results in an increased capacity for catheter adherence and bacterial interference. *Journal of Infectious Diseases* 2008, 198, 899-906.
Darouiche RO, et al. Multicenter Randomized Controlled Trial of Bacterial Interference for Prevention of Urinary Tract Infection in Patients With Neurogenic Bladder. *Urology* 2011, 78, 341-346.
Darouiche RO, Hull RA. Bacterial Interference for Prevention of Urinary Tract Infection. Clinical Infectious Diseases 2012, 55, 1400-1407.
Hull, RA, et al. Virulence properties of *Escherichia coli* 83972, a prototype strain associated with asymptomatic bacteriuria. Infection and Immunity 1999, 67, 429-432.
Lopez A, et al. Biofunctionalization of silicone polymers using poly(amidoamine) dendrimers and a mannose derivative for prolonged interference against pathogen colonization. *Biomaterials* 2011, 32, 4336-4346.
Pickard R, et al., Types of urethral catheter for reducing symptomatic urinary tract infections in hospitalised adults requiring short-term catheterisation: multicentre randomised controlled trial and economic evaluation of antimicrobial- and antiseptic-impregnated urethral catheters (the Catheter trial). *Health Technology Assessment* 2012, 16, No. 47.
Siddiq DM, Darouiche RO. New strategies to prevent catheter-associated urinary tract infections. *Nature Reviews Urology* 2012, 9, 305-314.

* cited by examiner

*Primary Examiner* — Amber D Steele
(74) *Attorney, Agent, or Firm* — Winstead PC

(57)    ABSTRACT

In an embodiment, the present disclosure pertains to a method and compositions for modification of medical devices, such as indwelling medical devices, implantable catheters, in particular, urinary catheters, to enhance formation of a high density and stable biofilm comprising non-pathogenic organisms for the treatment and prevention of colonization of pathogens leading to device-associated infections, such as urinary tract infections. In some embodiments the present disclosure also relates to a method and compositions for storage and use of the catheters coated with a non-pathogenic biofilm. In some embodiments the present disclosure also pertains to a method and compositions for modification of implantable medical devices with bacterial resistant polymers, and/or antimicrobial agents.

47 Claims, 12 Drawing Sheets

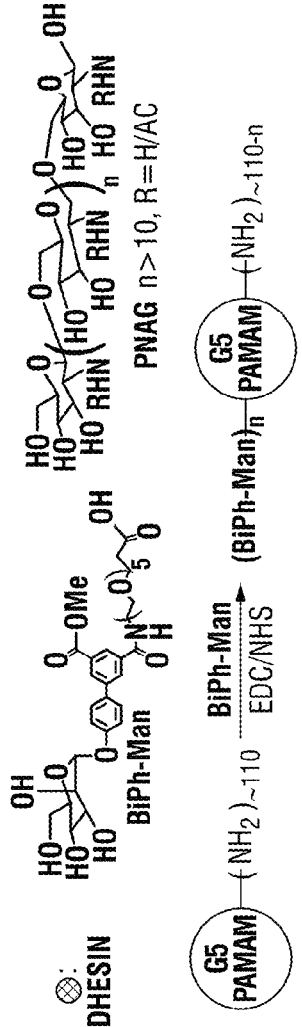
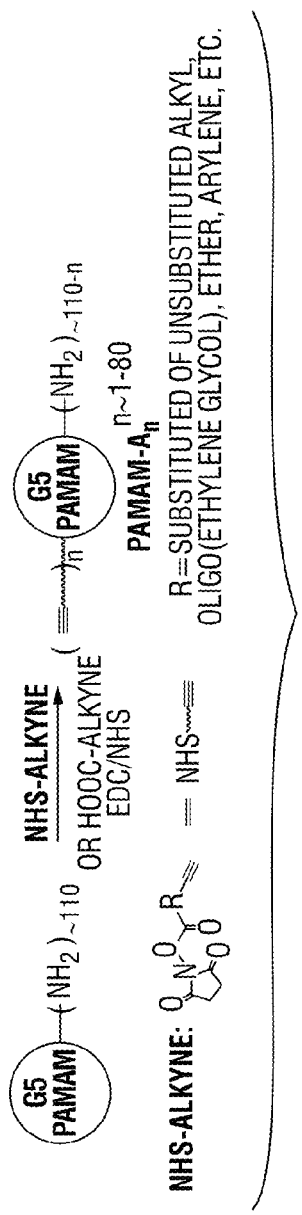
FIG. 2A
FIG. 2B

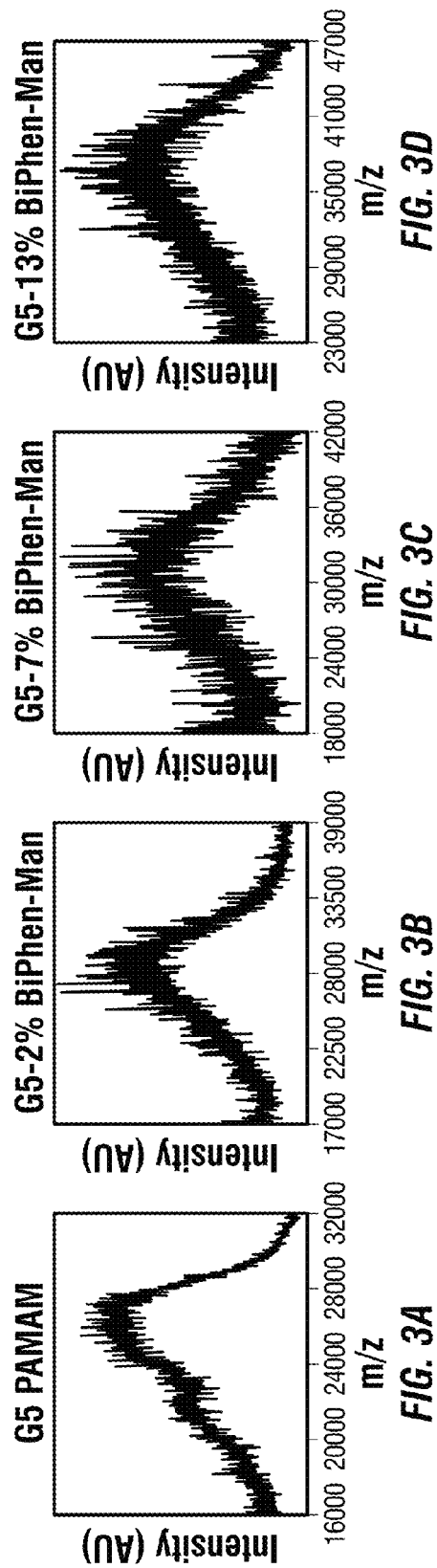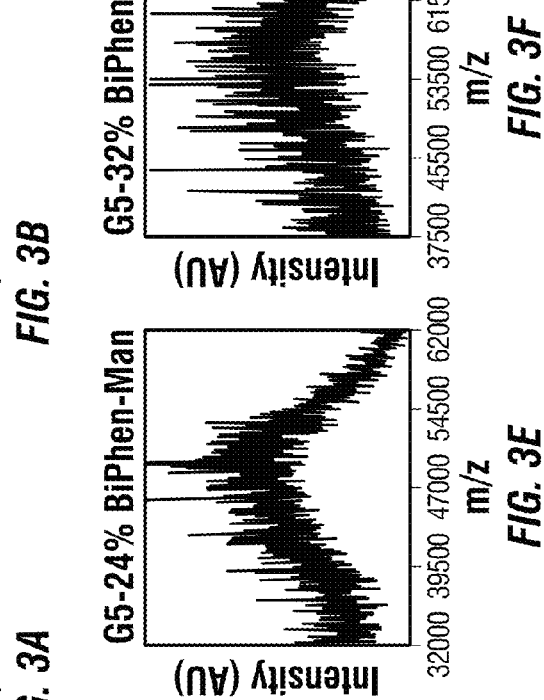
FIG. 3A FIG. 3B FIG. 3C FIG. 3D FIG. 3E FIG. 3F FIG. 3G

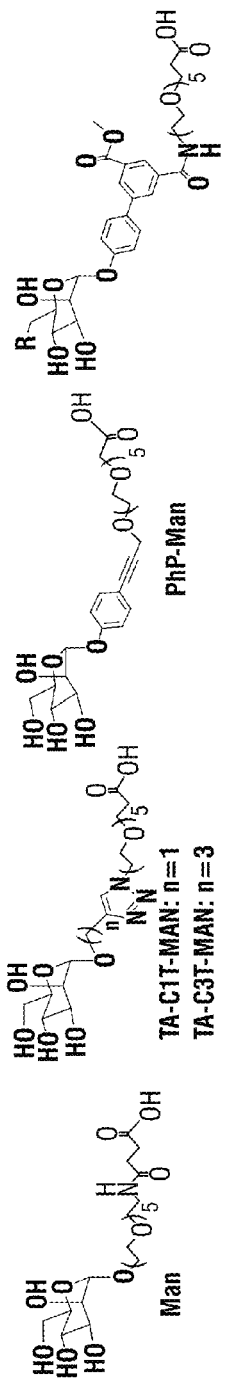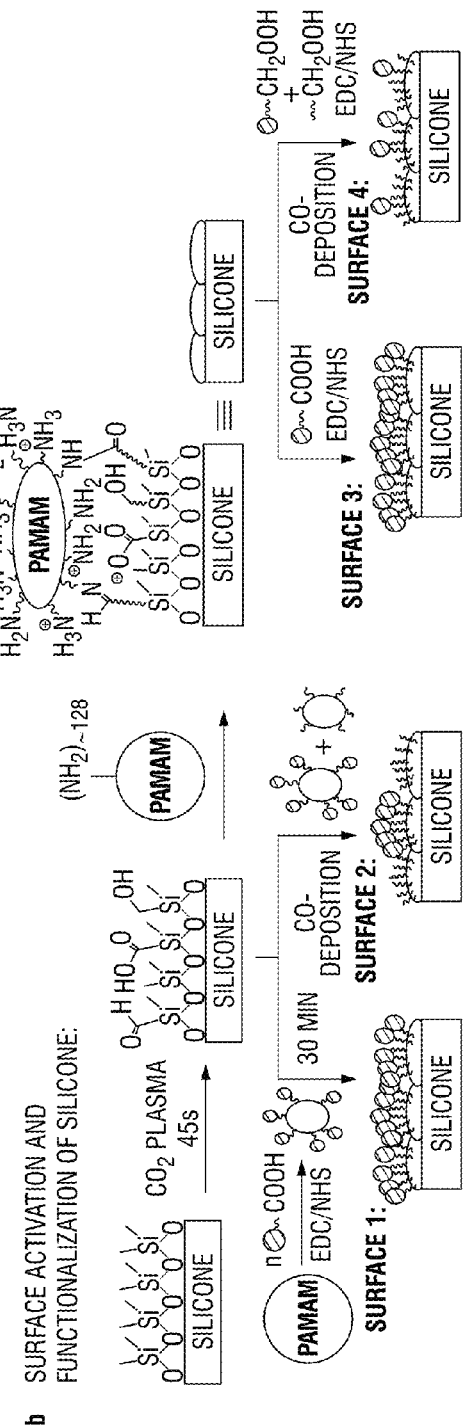
FIG. 4A
FIG. 4B

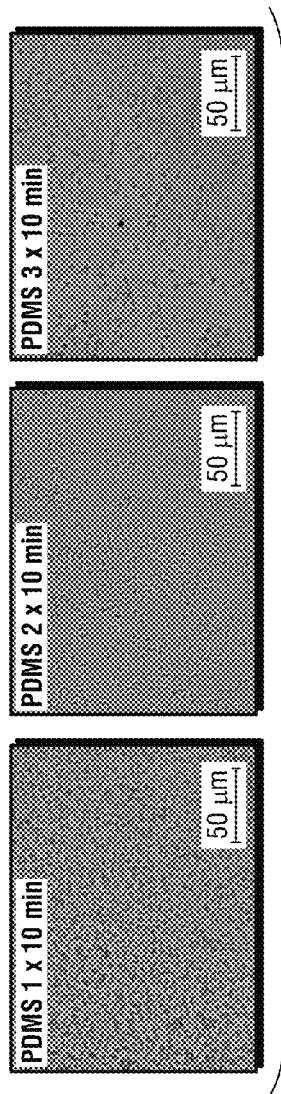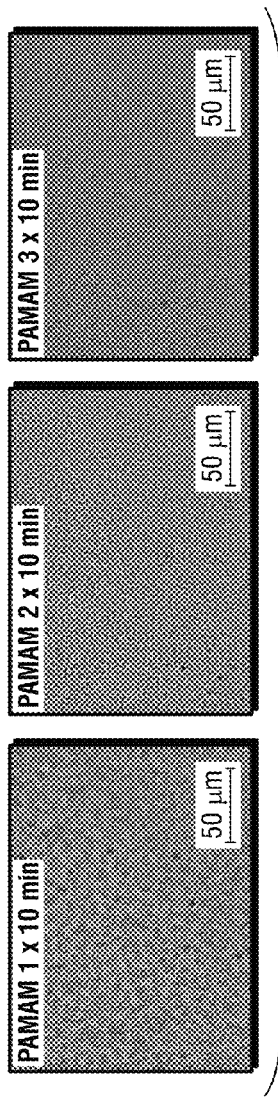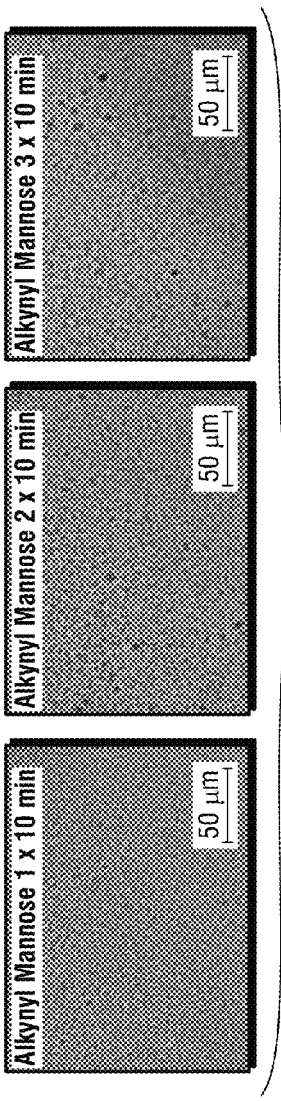

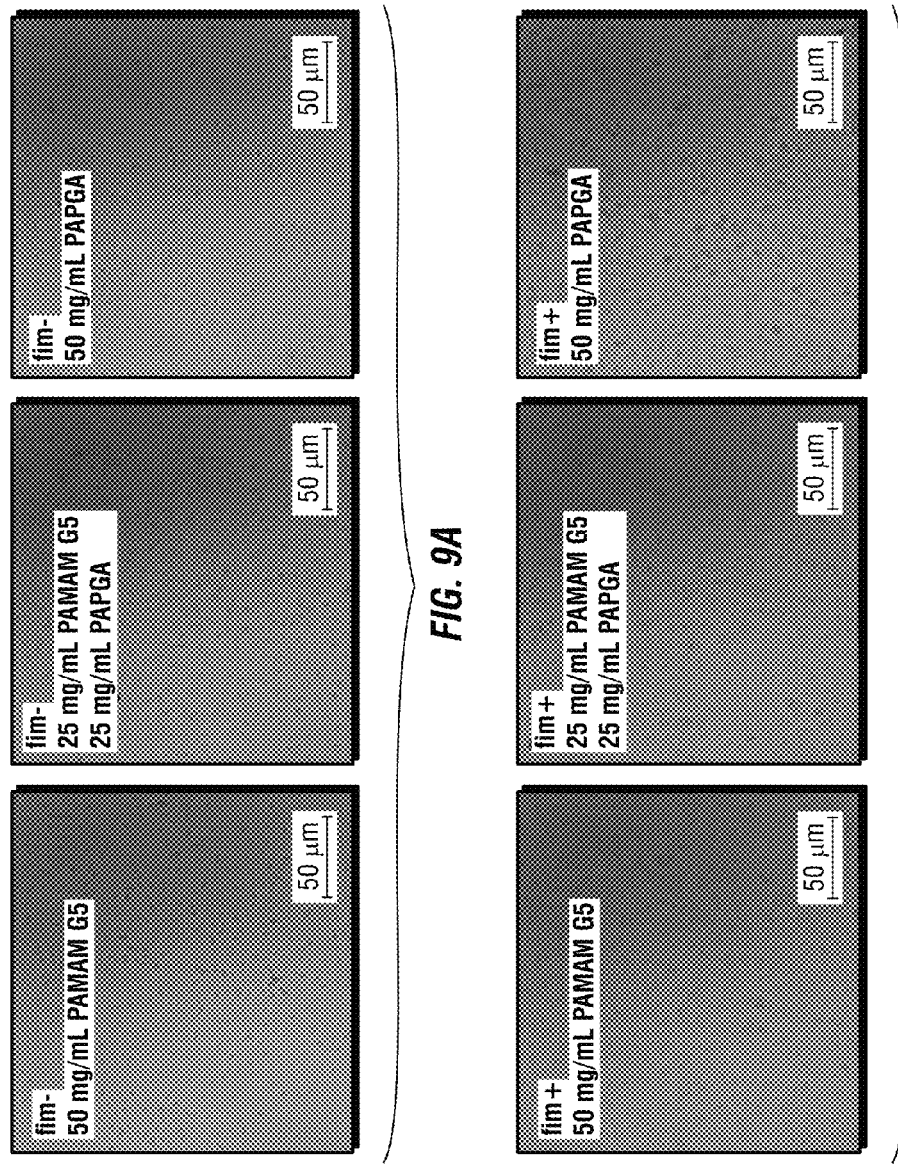

NON-PATHOGENIC BIOFILMS AND USES THEREOF

CROSS REFERENCE TO RELATED APPLICATIONS

This application claims priority to U.S. Provisional Patent Application No. 61/869,349, filed on Aug. 23, 2013. The entirety of the aforementioned application is incorporated herein by reference.

STATEMENT REGARDING FEDERALLY SPONSORED RESEARCH

The present invention was supported, in whole or in part, by National Science Foundation grants number DMR 1207583. The Government has certain rights in this invention.

BACKGROUND

A major problem associated with indwelling medical devices, for example catheters, is the formation of pathogenic biofilms on the surfaces of such devices. These highly resistant pathogenic biofilms contribute to the development of nosocomial infections that account for about 30-40% of the infections reported for acute care hospitals in the United States and affects millions of patients worldwide annually. Some of the current methods targeted at preventing pathogenic biofilm formation on such medical devices include, coating the indwelling device with antimicrobial compositions or forming an anti-fouling coating on the devices prior to insertion or implantation. These prior art methods and compositions are fraught with problems. For instance, antimicrobial agents are not effective because the pathogenic bacteria, in the biofilms formed on the indwelling devices, are embedded in a self-produced polymer matrix and are protected from the antimicrobial agents. Additionally, the anti-fouling coatings provide a short bacterial interference time as these are not stable in vivo and do not provide a high coverage of the surface to be protected. Hence, there exists a need in the art to develop compositions and methods that are effective in preventing the formation of pathogenic biofilms on indwelling medical devices.

SUMMARY

In some embodiments, the present disclosure relates to a method of making a modified silicone surface. Such a method comprises activating the silicone surface. In some embodiments, the method further comprises mixing a plurality of cross-linking dendrimers with a plurality of ligand derivatives to allow binding of dendrimers to ligand derivatives. In some embodiments, the method comprises functionalizing the silicone surface by immobilizing the plurality of the cross-linked dendrimers bound to the plurality of ligand derivatives on the activated silicone surface. In some embodiments, the plurality of cross-linking dendrimers comprise a dendrimeric moiety selected from the group consisting of poly(amido amine)polylysine, poly(amino acid), polyallylamine, polyamines, poly(proplyl imine), and combinations thereof. In some embodiments, the plurality of cross-linking dendrimers comprise a generation 5 poly (amido amine) dendrimer (G5 PAMAM). In some embodiments of the present disclosure, the ligand-derivatives, each comprises a bacterial adhesion molecule. In an embodiment of the present disclosure, the bacterial adhesion molecule is a mannose derivative. In another embodiment of the present disclosure, the bacterial adhesion molecule is poly-β-(1-6)-N-acetyl-D-glucosamine (PNAG). In some embodiments the method further comprises adhering a non-pathogenic biofilm to the modified silicone surface. In some embodiments, the functionalizing provides a ligand-presenting modified silicone surface conducive for the formation and accumulation of a non-pathogenic biofilm. In some embodiments, the modified silicone surface interferes with pathogen colonization.

In some embodiments, the present disclosure pertains to a modified silicone surface. In some embodiments, the modified silicone surface comprises a plurality of the cross-linked dendrimers bound to a plurality of ligand derivatives immobilized on the silicone surface to form a functionalized ligand-presenting silicone surface. In some embodiments, a non-pathogenic biofilm is adhered to the functionalized ligand-presenting silicone surface. In some embodiments, the modified silicone surface interferes with pathogen colonization. In some embodiments, the silicone surface is activated to immobilize the plurality of the cross-linked dendrimers bound to a plurality of ligand derivatives on the silicone surface. In some embodiments, the plurality of cross-linking dendrimers comprise a dendrimeric moiety selected from the group consisting of poly(amido amine) polylysine, poly(amino acid), polyallylamine, polyamines, poly(proplyl imine), and combinations thereof. In some embodiments, the plurality of cross-linking dendrimers comprise a generation 5 poly(amido amine) dendrimer (G5 PAMAM). In some embodiments of the present disclosure, the ligand-derivatives, each comprises a bacterial adhesion molecule. In an embodiment of the present disclosure, the bacterial adhesion molecule is a mannose derivative. In another embodiment of the present disclosure, the bacterial adhesion molecule is poly-β-(1-6)-N-acetyl-D-glucosamine (PNAG). In some embodiments, the activation of the silicone surface comprises oxidizing the silicone surface. In some embodiments, the oxidizing preferably comprises $CO_2$ plasma treatment.

In some embodiments, the present disclosure pertains to a method of preventing pathogenic colonization of a silicone surface. Such a method comprises functionalizing the silicone surface. In some embodiments, the method further comprises adhering a non-pathogenic biolfilm to the functionalized silicone surface. In some embodiments, the functionalizing comprises activating the silicone surface. In some embodiments, the functionalizing comprises mixing a plurality of cross-linking dendrimers with a plurality of ligand derivatives to allow binding of dendrimers to ligand derivatives. In some embodiments, the functionalizing further comprises immobilizing the bound dendrimer-ligand complexes on the silicone surface. In some embodiments, the functionalizing provides a ligand-presenting modified silicone surface conducive for the formation and accumulation of the non-pathogenic biofilm.

In some embodiments, the plurality of cross-linking dendrimers comprise a dendrimeric moiety selected from the group consisting of poly(amido amine)polylysine, poly (amino acid), polyallylamine, polyamines, poly(proplyl imine), and combinations thereof. In some embodiments, the plurality of cross-linking dendrimers comprise a generation 5 poly(amido amine) dendrimer (G5 PAMAM). In some embodiments, the ligand-derivatives, each comprises a bacterial adhesion molecule. In an embodiment of the present disclosure, the bacterial adhesion molecule is a mannose derivative. In another embodiment of the present disclosure, the bacterial adhesion molecule is poly-β-(1-6)-N-acetyl-D-glucosamine (PNAG).

In an embodiment, the present disclosure pertains to a method and compositions for modification of medical devices, urinary catheters, to enhance formation of a high density and stable biofilm comprising non-pathogenic organisms for the treatment and prevention of colonization of pathogens leading to device-associated infections. In some embodiments of the present disclosure the medical device is an indwelling medical device. In an embodiment, the indwelling medical device is an implantable catheter. In some embodiments of the present disclosure the device-associated infection is a urinary tract infection. In some embodiments the present disclosure also relates to a method and compositions for storage and use of the catheters coated with a non-pathogenic biofilm. In some embodiments the present disclosure also pertains to a method and compositions for modification of implantable medical devices with bacterial resistant polymers, and/or antimicrobial agents.

BRIEF DESCRIPTION OF THE DRAWINGS

FIGS. 2A-2C show examples for the preparation of PAMAM-adhesin conjugates. FIG. 2A shows preparation of BiPh-Man-PAMAM conjugates with various density of the mannoside on PAMAM; FIG. 2B shows preparation of PAMAM-alkyne conjugates with various density of the alkynyl groups on PAMAM; and FIG. 2C shows preparation of PNAG-azide conjugates and the coupling with PAMAM-alkyne via copper-catalyzed alkyne-azide cycloaddition reaction to form the PNAG-PAMAM conjugates;

FIGS. 3A-3G show MALDI-TOF mass spectra of unmodified and mannosylated G5 PAMAM dendrimers;

FIGS. 4A-4B show a series of mannosides ligands with various binding affinities to fimH (FIG. 4A), and the process for immobilization of them to provide Surfaces 1-4 with a nanoscale control of the local versus global density involving activation of silicone with $CO_2$ plasma followed by direct deposition of mannoside-coated PAMAM to provide Surfaces 1 and 2 or by modification with G5-PAMAM and then deposition of mannosides to provide Surfaces 3 and 4. The average global versus local density in these surfaces can be controlled over a wide range by co-deposition at desired ratio of the functional molecules versus inert molecules (FIG. 4B);

FIGS. 6A-6C show stability of fim+E. coli 83972 on PDMS (FIG. 6A), unmodified PAMAM (FIG. 6B) and Phen-Man (mannosylated G5 PAMAM)(FIG. 6C) surface after shaking for various times. The images were taken after the samples were shaken for 10 min, 2×10 min and 3×10 min in AU by Nikon microscopy under reflected bright field;

FIG. 7B is a plot of the areas covered by E. faecalis on the indicated surfaces with (gray) or without (green) pre-treatment with fim+E. coli 83972. The data represent the mean of at least 2 experiments where 10 fields were imaged for each surface. FIG. 7C shows a plot of the colony counts following a challenge with (grey bar) or without (green bar) E. coli 83972 biofilms on BiPh-Man surface after culture at a high pathogen concentration ($10^8$ CFU/ml) in LB for 11 days. The remaining E. coli 83972 is represented by the pink bars.

FIGS. 9A-9B show coating of wild-type E. coli 83972 (fim-)(FIG. 9A) and fim+E. coli 83972 mutant HU2425 (fim+)(FIG. 9B) on $CO_2$ plasma treated silicone surfaces with and without treatment with PNAG (equivalent to PAPGA). PDMS surface was activated by $CO_2$ for 45 s. Then the surfaces were incubated in solutions of G5 PAMAM (50 mg/mL), G5 PAMAM+PNAG (25 mg/mL+25 mg/mL) and PNAG (50 mg/mL) (10 μL/cm2) for 2 h and washed copiously with water. E. coli 83972 with or without fimbriae (OD600=0.25) were incubated with the surface for 5 days at 37° C. The result shows that simply applying PNAG as an bacterial extract onto the silicone surface does not promote the wild-type E. coli 83972 biofilm formation.

DETAILED DESCRIPTION

Figure 1:
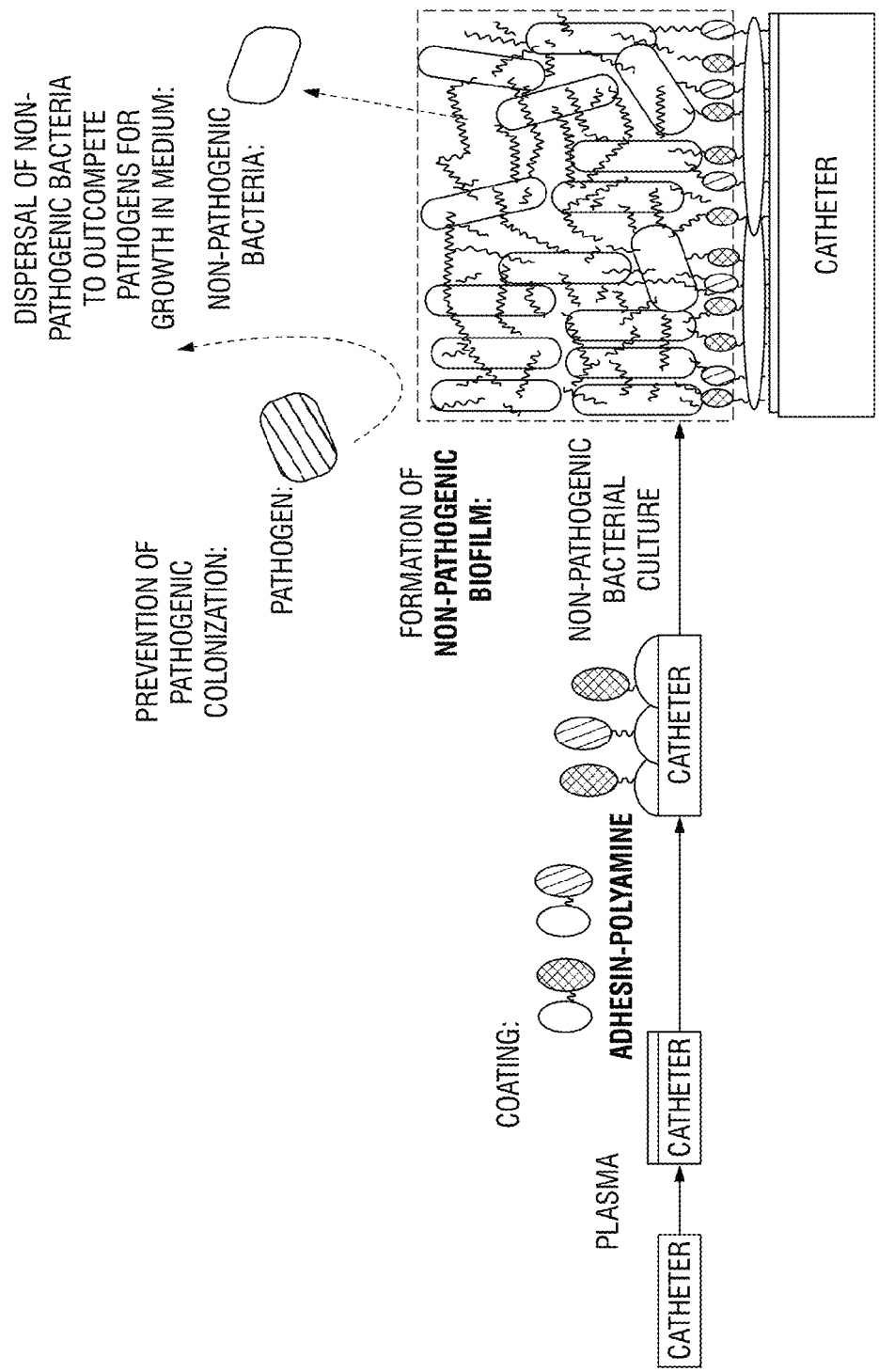
FIG. 1 depicts an overview of a method and composites for surface modification to enhance formation of a non-pathogenic biofilm on a medical device for inhibition of pathogenic colonization and growth.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Biofilms are defined as group of microorganisms in which cells stick to each other and bind on a surface through matrix of extracellular polymeric substance (EPS). The microbial cells growing in a biofilm are physiologically distinct from planktonic cells of the same organism, which, by contrast, are single-cells that may float or swim in a liquid medium. Stable biofilms do not easily detach from the surface when subjected to normal in vivo physiological conditions, such as under urinary flow, or in vitro assays simulating in vivo conditions, such as incubation with rocking/shaking or under a flow with a proper speed. Under physiological conditions in a nutrient-rich medium such as urine, biofilms continuously disperse planktonic cells of the same organism into the medium, which can colonize on new locations, such as bladder, and compete with other organisms for growth in the medium. Hence, biofilms are effective in mediating bacterial interference and thus prevent pathogenic colonization of biofilm coated surfaces.

Numerous challenges exist in forming a stable and high coverage non-pathogenic biofilm. Specifically, the formation of biofilms on indwelling medical devices that can withstand physiological conditions over a long period of time has been challenging. Previous approaches have included applying a non-pathogenic bacterial coating layer to a medical device. The non-pathogenic bacterial culture is prepared on site from a kit comprising a culture of non-pathogenic bacterium which may be lyophilized for storage. The non-pathogenic bacterial coating layer formed as a result is not a biofilm, and is difficult to grow into a biofilm, especially for a short period of time (after applying the bacterial culture by the healthcare professionals and before insertion the coated catheter into patient's urinary tract). In view of these limitations, these methods have a low chance of establishing a high coverage and stable non-pathogenic biofilm on the medical device.

Escherichia coli 83972 is the most extensively tested non-pathogenic bacteria against catheter-associated urinary tract infections (CAUTI). It was originally isolated from a young woman in Sweden, who carried it for at least three years without urinary tract infection symptom. Wild-type E. coli 83972 expresses none of the functional pili (fimbriae) and thus has a low adherence both on urinary catheters and bladder. The method used in the clinical trial for installation of wild-type E. coli 83972 against CAUTI involves injection of the bacteria via the inserted catheter into patient's bladder. This method is tedious and expensive and has a low success rate that limited the overall efficacy. Specifically, the bacteria were injected via the catheter into the bladder and the catheter was clamped for 1 hour before draining, and afterwards these steps were repeated. The procedure was repeated on three consecutive days to complete one inoculation cycle. In one study, it was reported that only ~24% and ~36% of the male patients retained the bacteria for 4 weeks after one and two inoculation cycles, respectively. In another study, for unknown reasons, all female patients failed to retain the bacteria for 4 weeks.

The overall efficacy for treatment with injected E. coli 83972 is limited by the low retention rate of the non-pathogenic bacteria. The limitation of introducing the non-pathogenic bacteria after catheter insertion can be attributed to the fact that the non-pathogenic bacteria (generally lack of fimbriae) are sluggish to form biofilms on the catheter surfaces. Therefore, they cannot prevent pathogens from establishing and growing colonies and biofilms on the catheter, which are a source of constant dispersal of pathogens to attack the bladder.

In contrast, bacteria expressing fimbriae are able to adhere to the surface better to form a biofilm but fimbriae are generally considered virulence factors, rendering the use of modified benign bacteria a risky practice. Accordingly, while several clinical trials involving hundreds of patients have been carried out in the U.S., using wild type E. coli 83972, none of these clinical studies used fim+ E. coli 83972 mutants, expressing fimbriae. In the industrialized countries, only one clinical study using fim+ E. coli 83972 mutants, expressing fimbriae, has been reported.

Another approach of preventing pathogenic colonization involves coating of a catheter with non-pathogenic bacteria by applying a culture of the non-pathogenic bacteria directly to the catheter prior to inserting it to the patient's urinary tract. See U.S. Pat. Nos. 7,790,183 and 6,719,991, and EP1303256, 2009. However, this method has a relatively low chance of establishing a high coverage and stable non-pathogenic biofilm on the catheter. In fact, after 2 day incubation of silicone catheters in a culture of an E. coli 83972 mutant (strain HU2545) expressing type 1 fimbriae, which enhance its adherence to the catheter, less than 50% of the surface was covered by the bacteria. Further, the E. coli 83972 mutant (strain HU2545) expressing type 1 fimbriae bind weakly to unmodified silicone surfaces and most of them are easily removed after shaking at 200 rpm for 20 min in artificial urine (FIG. 6).

In contrast, when the modified silicone substrate disclosed herein was incubated in culture of the same E. coli 83972 mutant, under the same conditions, it resulted in the formation of greater coverage and highly stable biofilms that fully covered the modified silicone surface, and remained stable after shaking at 200 rpm for 120 min. Furthermore, the performance of bacterial interference of the biofilms of the E. coli 83972 mutant (HU2545), formed by the methods disclosed herein, directly correlate with the coverage of the biofilm on the silicone surface. For example, upon comparison of the coating of HU2545 on unmodified silicone (control group) and on silicone modified with the methods disclosed herein (experimental group), under similar challenges with mixtures of clinical isolates under the same conditions, fewer uropathogens were found on the biofilms of the experimental group. In contrast, in the control group the uropathogens nearly completely took over the surface (See Example 12).

Moreover, in the experimental group, the E. coli 83972 biofilms continuously dispersed the planktonic cells into the media, thereby effectively inhibiting the growth of the uropathogens in the medium. Hence, the catheters and medical devices coated with an E. coli 83972 biofilm using the methods and composites, disclosed herein eliminates the need for performing the aforementioned tedious procedure for installation of E. coli 83972 into a patient's bladder. Additionally, because the stable biofilms of the present disclosure continuously disperse planktonic cells into urine, the success rate for preventing bladder colonization is expected to greatly improve. Furthermore, both the pathogenic colonization on the catheter and growth in the urine are effectively reduced by the E. coli 83972 biofilm on the catheter and the planktonic E. coli 83972 dispersed from the biofilm, respectively.

In general, modification of the surface of the medical device, using the methods and compositions of the present disclosure, allows for the formation of high stability non-pathogenic biofilm with higher surface area coverage resulting in a higher effectiveness in prevention of pathogenic colonization of the medical device.

In some embodiments, the present disclosure relates to a method of making a modified silicone surface. Such a method comprises activating the silicone surface. In some embodiments the method further comprises mixing a plurality of cross-linking dendrimers with a plurality of ligand derivatives to allow binding of dendrimers to ligand derivatives. In some embodiments, the method comprises functionalizing the silicone surface by immobilizing the plurality of the cross-linked dendrimers bound to the plurality of ligand derivatives on the activated silicone surface. In some embodiments the method further comprises adhering a non-pathogenic biolfilm to the modified silicone surface. In some embodiments, the functionalizing provides a ligand-presenting modified silicone surface conducive for the formation and accumulation of a non-pathogenic biofilm. In some embodiments, the modified silicone surface interferes with pathogen colonization.

Without being bound by theory, in some embodiments, the activation comprises oxidizing the silicone surface. In some embodiments, the oxidizing preferably comprises $CO_2$ plasma treatment. In some embodiments, the treatment with $CO_2$ plasma is for about 5 s to about 300 s. In some embodiments, the treatment with $CO_2$ plasma is for about 30 s to about 60 s. In some embodiments, the treatment with $CO_2$ plasma is at a low power setting. In some embodiments, the power setting ranges from about 1 W to about 10 W.

In some embodiments, the activated silicone surface comprises substituted poly(dimethylsiloxane) of the general formula —[O—Si($CR^1R^2$)]$_n$—, where $R_1$ and $R_2$ may be an alkyl, ethers, esters, amides, or a combination thereof. In some embodiments, the alkyl is a methyl, butyl, hexyl, or a combination thereof. In some embodiments, the activated silicone surface further comprises fluorocarbons.

In some embodiments, the functionalization of the activated silicone surface is by immersing the activated silicone surface in a first solution. In some embodiments, the first solution comprises a plurality of cross-linked dendrimers. In some embodiments, the plurality of cross-linked dendrimers comprise generation 5 poly(amido amine) dendrimer (G5 PAMAM). In some embodiments, the silicone surface is functionalized with 5 poly(amido amine) dendrimer (G5 PAMAM) In some embodiments the silicon surface functionalized with 5 poly(amido amine) dendrimer (G5 PAMAM) is immersed in a second solution. In some embodiments, the second solution comprises a plurality of ligand derivatives and an activating agent. In some embodiments, the activating agent comprises 1-ethyl-3-(3-dimethylaminopropyl) carbodiimide hydrochloride and N-hydroxysuccinimide.

In some embodiments, the solution comprises the plurality of the cross-linked dendrimers bound to the plurality of ligand derivatives. In some embodiments, the solution comprises mannosylated-generation 5 poly(amido amine) dendrimer (G5 PAMAM). In some embodiments the ratio of the mannose to the G5-PAMAM ranges from about 2:1 to about 60:1. In some embodiments, the solution comprises the plurality of cross-linked dendrimers bound to the plurality of ligand derivatives and unmodified cross-linked dendrimers. In some embodiments the solution comprises mannosylated-G5 PAMAM and unmodified G5 PAMAM.

In some embodiments of the present disclosure, the plurality of cross-linking dendrimers comprise an amidation product of the amino-terminus of an amino-terminated cross-linking dendrimer. In some embodiments, the plurality of cross-linked dendrimers comprise dendrimers terminated with multiple amino groups. In some embodiments, the plurality of cross-linked dendrimers comprise polyamines. In some embodiments, the plurality of cross-linking dendrimer comprise a dendrimeric moiety selected from the group consisting of poly(amido amine)polylysine, poly (amino acid), polyallylamine, polyamines, poly(proplyl imine), and combinations thereof. In some embodiments, the plurality of cross-linking dendrimers comprise a generation 5 poly(amido amine) dendrimer (G5 PAMAM).

In some embodiments of the present disclosure, the plurality of ligand derivatives comprise an amidation product of a carboxylic acid terminal group. In some embodiments, the ligand-derivatives, each comprises a bacterial adhesion molecule. In an embodiment of the present disclosure, the bacterial adhesion molecule is a mannose derivative. In another embodiment of the present disclosure, the bacterial adhesion molecule is poly-β-(1-6)-N-acetyl-D-glucosamine (PNAG). In some embodiments, the mannose derivatives are selected from BiPh-Man, PhP-Man, TA-C3T-Man, Man, TACIT-Man, BiPh-F-Man.

In some embodiments, the ligand derivatives further comprise an oligo(ethylene)glycol linker bound via a glycosidic linkage. In some embodiments, the ligand derivative further comprises a moiety bonded to the oligo(ethylene) glycol linker. In some embodiments, the moiety is selected from the group consisting of phenyl, alkylphenyl, biphenyl, fluorinated biphenyl, hydroxylated biphenyl, and trizolylalklyl.

In some embodiments, the mixing of the plurality of ligand derivatives with the plurality of cross-linked dendrimers is in the ratio ranging from about 2:1 to about 60:1.

In some embodiments of the present disclosure, the plurality of ligand derivatives are mixed with an activating agent prior to mixing with the plurality of the cross-linking dendrimers. In some embodiments, the activating agent comprises 1-ethyl-3-(3-dimethylaminopropyl) carbodiimide hydrochloride and N-hydroxysuccinimide. In some embodiments, the plurality of cross-linked dendrimers are allowed to bind to the plurality of ligand derivatives before being immobilized on the activated silicone surface. In some embodiments, the plurality of cross-linked dendrimers are co-deposited with the plurality of ligand derivatives. In some embodiments, the unreacted groups on the plurality of cross-linked dendrimers are capped following binding of the plurality of ligand derivatives.

In some embodiments of the present disclosure, the non-pathogenic biofilm comprises a plurality of bacteria. In some embodiments of the present disclosure the non-pathogenic biofilm comprises known non-pathogenic bacteria. In some embodiments, the non-pathogenic biofilm comprise pathogenic bacteria that have been mutated or converted to non-pathogenic strains. In some embodiments, the non-pathogenic bacteria for biofilm formation may be selected from the group consisting of Enterobacteriacea (e.g. *Escherichia, Salmonella* and *Yersinia*), *Pseudomonas aeruginosa, Stenotrophomonas maltophilia, Burkholderia cepacia, Gardnerella vaginalis* and *Acinetobacter* species. In an exemplary embodiment, the bacteria comprise *E. coli* 83972. In some embodiments, the bacteria comprise fim+ *E. coli* mutant strain HU2425.

In some embodiments, the present disclosure pertains to a modified silicone surface. In some embodiments, the modified silicone surface comprises a plurality of the cross-linked dendrimers bound to a plurality of ligand derivatives immobilized on the silicone surface to form a functionalized ligand-presenting silicone surface. In some embodiments, the silicone surface is activated to immobilize the plurality of the cross-linked dendrimers bound to a plurality of ligand derivatives. In some embodiments, the activation of the silicone surface comprises oxidizing the silicone surface. In some embodiments, the oxidizing preferably comprises $CO_2$ plasma treatment. In some embodiments, a non-pathogenic biolfilm may be adhered to the functionalized ligand-presenting silicone surface. In some embodiments, the modified silicone surface interferes with pathogen colonization.

In some embodiments, the present disclosure pertains to a method of preventing pathogenic colonization of a silicone surface. Such a method comprises functionalizing the silicone surface. In some embodiments, the method comprises adhering a non-pathogenic biofilm to the functionalized silicone surface. In some embodiments, the functionalizing comprises activating the silicone surface. In some embodiments, the functionalizing comprises mixing a plurality of cross-linking dendrimers with a plurality of ligand derivatives to allow binding of dendrimers to ligand derivatives. In some embodiments, the functionalizing comprises immobilizing the plurality of the cross-linked dendrimers bound to the plurality of ligand derivatives on the activated silicone surface. In some embodiments, the functionalizing provides a ligand-presenting modified silicone surface conducive for the formation and accumulation of the non-pathogenic biofilm.

In some embodiments, the silicone surface is that of an indwelling medical device. In some embodiments, the indwelling medical device is an implantable catheter. In some embodiments, the implantable catheter is a central venous catheter, a peritoneal dialysis catheter, or a urinary catheter. In some embodiments, the indwelling medical device is a mechanical heart valve, or voice prosthesis. In some embodiments, the indwelling medical device is a urinary catheter.

In an embodiment the present disclosure relates to methods and compositions for coating of medical devices with a stable non-pathogenic biofilms, followed by lyophilizing and packaging of the medical device for long-term storage. In an embodiment, the medical device is a catheter. In some embodiments, the medical device is an indwelling device. The non-pathogenic biofilms are used to prevent or greatly reduce nosocomial infections associated with long-term placement of the medical device in a subject. In an embodiment of the present disclosure, the non-pathogenic biofilms are used to prevent or greatly reduce device-associated infections. For instance, catheter-associated urinary tract infection (CAUTI), is the most common hospital-acquired infections in the United States. CAUTI is caused by the pathogenic colonization and biofilm formation on the urinary catheters. Given the high occurrence rate of CAUTI (3%-10%) per day, prevention is preferred over treatment with antibiotics.

In an embodiment, the present disclosure pertains to compositions and methods for surface modification of catheters and other medical devices to allow for the formation of a high coverage and stable non-pathogenic biofilm coating on the medical device to prevent pathogen colonization prior to placement of the medical device in a subject in need thereof. In some embodiments, the present disclosure relates to inhibiting pathogenic colonization on the surfaces of such devices using non-pathogenic biofilms coated on medical devices. The coverage and stability of the non-pathogenic biofilm determines the effectiveness against pathogenic colonization.

Most implantable medical devices, for instance, catheters are made of silicone elastomers. Silicone is composed of mainly polydiakylsiloxane, especially polydimethylsiloxane (PDMS), an inert hydrophobic polymer. Covalent functionalization of these elastomers requires activation with high energy species such as radicals to generate active groups on the material surfaces. The present disclosure pertains to a method of activating the silicone surfaces to achieve the required covalent functionalization to facilitate the formation of high surface area coverage and stable non-pathogenic biofilms. Methods of activation for covalent functionalization of silicone elastomers, to enhance and facilitate the formation of high surface area coverage and stable non-pathogenic biofilms are also disclosed in US20120231518, which is incorporated herein by reference in its entirety. In an embodiment, the method of activation to achieve covalent functionalization pertains to combining $CO_2$ plasma treatment of silicone elastomers and the use of a plurality of dendritic polyamine derivatives, such as polyamidoamine (PMAM) dendrimer, to cross-link the activated silicone polymer. In an embodiment, the method also relates to attaching one or multiple functional moieties, such as bacterial adhesion molecules, including mannosides and partially deacetylated poly-$\beta$-(1-6)-N-acetyl-D-glucosamine (PNAG), either before or after the deposition onto the covalently functionalized silicone elastomer.

Conventional methods for surface activation of silicone elastomers are based on $O_2$ plasma, which is a harsher method as compared to methods of surface activation using $CO_2$ plasma, and results in the fragmentation of the silicone chains. The short polymer chains with activated groups are more easily diffused away from the surface. To reduce this loss, immediately after the plasma treatment the surface is treated with dendritic polyamines, such as G5 PAMAM dendrimers containing ~128 peripheral amino groups. The reaction produces a stable extensively cross-linked network between the dendrimers and the activated PDMS polymer chains on the silicone substrate. In some embodiment the present disclosure pertains to methods of forming long-term stable non-pathogenic biofilms on silicone surfaces comprising using a combination of activation of silicone surface using $CO_2$ plasma and cross-linking the thus covalently functionalized surface using PAMAM dendrimers.

Hence, in some embodiments, the present disclosure relates to an efficient method for activation and functionalization of the inert surface of silicone elastomers, which largely enhance the formation of high coverage and stable non-pathogenic biofilms effective in inhibiting pathogenic colonization of medical devices. In some embodiments, this method is a combination of $CO_2$ plasma treatment of catheter or medical device surfaces and the use of dendritic polyamines derivatives tethering with one or multiple bacterial adhesion molecules, such as polyamidoamine (PAMAM) dendrimer derivatives tethering with partially deacetylated poly-$\beta$-(1,6)-N-acetyl-D-glucosamine (PNAG), to cross-link the activated silicone polymers. In an embodiment, the most common method for surface activation of silicone elastomers comprises $O_2$ plasma, resulting in more degradation of the silicon polymer as compared to $CO_2$ plasma. Although one study of coating of PAMAM dendrimer on $O_2$ plasma treated silicone has been reported (Cha 2001), the report did not specify the use of PAMAM for cross linking of partially degraded silicone polymers, and the combination of the mild $CO_2$ plasma treatment with the use of PAMAM dendrimers to cross link the partially degraded silicone polymers has not been reported. This present disclosure utilizes the combination of the mild $CO_2$ plasma with the use of PAMAM dendrimers to cross link the silicone polymers with active carbonyl groups generated from $CO_2$ plasma. The aforementioned method greatly enhances the stability of the functionalized surface. Thus, immediately after $CO_2$ plasma, the active carbonyl groups formed on the PDMS polymer bind with the PAMAM dendrimers containing ~128 amino groups, thereby avoiding substantial loss of the activated groups on the silicone polymer through diffusion or rearrangement. Instead, PAMAM dendrimers form a stable, extensively cross-linked network with the PDMS polymer. The resultant surface presenting PAMAM at a density of $2\times1012/cm^2$ is stable for over 5 weeks in PBS at 37° C., as confirmed by monitoring the XPS N1 s signal arisen from the PAMAM on the top surface.

In an embodiment, the present disclosure relates to a method and composites for modification of silicone surfaces to enhance the formation of high density and stable biofilms comprising potentially safer non-pathogenic bacteria that cannot produce fimbriae. Bacterial fimbriae are major adhesin that enhance biofilm formation but are also widely conceived virulence factors. Previous methods have reported the use of *E. coli* Nissle 1917 and an *E. coli* 83972 mutant strain HU2545. Both *E. coli* strains can produce type 1 fimbriae that are potential virulence factors. Although *E. coli* Nissle 1917 has been in the market as a probiotics for 50 years, there has been only one report of using this strain for prevention of urinary tract infection. In an embodiment, the present disclosure uses the wild-type *E. coli* 83972 that cannot produce type 1 fimbriae that are widely regarded as virulence factors. Wild-type *E. coli* 83972 is the only strain used in all clinical trial in the US; on contrary, only one clinical trial using *E. coli* 83972 mutant strain HU2545 has been reported, which was conducted in Sweden. Therefore, the wild-type *E. coli* 83972 biofilm coated urinary catheters in this invention are more likely to be approved for clinical trials than the catheters coated with *E. coli* 83972 mutant strain HU2545 as disclosed in US20120231518 A1, WO2012125576A1, 2012; incorporated herein by reference in its entirety. Notably, the composites for coating of biofilms of wild-type E. coli 83972 (lack of type-1 fimbriae) on silicone catheters are substantially different from those for coating of biofilms of E. coli 83972 mutant strain HU2545 (expressing type-1 fimbriae) described in US20120231518.

The methods and compositions of the present disclosure are amendable for large-scale and cost-effective coating of wild-type E. coli 83972 on catheter surfaces. Simply applying PNAG as a bacterial extract onto the silicone surface does not promote the wild-type E. coli 83972 biofilm formation.

In a wider scope, the present disclosure relates to practical methods and compositions for biofunctionalization of biomedical devices in general. For example, the method can be used for modification of medical devices, such as indwelling catheters used for dialysis or urinary drainage (e.g., intravenous, intraperitoneal, or intravesicular) with antibiofouling polymers, and/or antimicrobial agents. The coatings disclosed herein significantly decrease protein adsorption and when compared to medical silicone and/or other materials in use today. Therefore, the methods and compositions disclosed herein significantly decrease inflammatory, bacterial and fungal cell adherence. For these applications, long-term stability of the antifouling and antibacterial coating is crucial. The present disclosure addresses this critical need.

In some embodiments, the present disclosure pertains to a medical device with a modified silicone surface comprising an activated silicone layer, a plurality of activated dendrimers absorbed on to the activated silicone layer; a plurality of ligand derivatives, each bound to at least one of the plurality of cross-linked dendrimers; and a non-pathogenic biofilm adhered to the plurality of ligand derivatives. In some embodiments, the modified silicone surface contributes to the inhibition of pathogen colonization and growth. In an embodiment, the cross-linked dendrimers each comprise an amidation product of the amino-terminus of an amino-terminated cross-linking dendrimer. In some embodiments, the amino-terminated dendritic polymer is the G5 PAMAM. In an embodiment, the ligand-derivative, each comprises a bacterial adhesion molecule. In an embodiment of the present disclosure, the bacterial adhesion molecule is a mannose derivative. In another embodiment of the present disclosure, the bacterial adhesion molecule is PNAG. In some embodiments the non-pathogenic biofilm comprises a plurality of bacteria. In an embodiment, the bacteria comprise Escherichia Coli. In some embodiments the Escherichia. Coli lack fimbriae. In an embodiment, the bacterium is Escherichia Coli 83972. In some embodiments the medical device is a catheter. In some embodiments the non-pathogenic biofilm is highly stable in vivo and in vitro. In an embodiment, the non-pathogenic biofilm provides high surface coverage of the medical device. In some embodiments the non-pathogenic biofilm is able to provide prolonged pathogenic bacterial interference.

In some embodiments, the present disclosure pertains to a method of coating a silicone surface of a medical device with a non-pathogenic biofilm comprising attaching a plurality of ligand-derivatives to a plurality of cross-linked dendrimers; activating the silicone surface of a medical device; adsorbing the plurality of cross-linked dendrimers bound to the plurality of ligand-derivatives to the activated silicone surface; and adhering a non-pathogenic biofilm to the plurality of ligand derivatives. In an embodiment, the cross-linked dendrimers each comprise an amidation product of the amino-terminus of an amino-terminated cross-linking dendrimer. In some embodiments, the amino-terminated dendritic polymer is the G5 PAMAM. In an embodiment, the ligand-derivative each comprises a bacterial adhesion molecule. In an embodiment of the present disclosure, the bacterial adhesion molecule is a mannose derivative. In another embodiment of the present disclosure, the bacterial adhesion molecule is PNAG. In some embodiments the non-pathogenic biofilm comprises a plurality of bacteria. In an embodiment, the bacteria comprise Escherichia Coli. In some embodiments the Escherichia. Coli lack fimbriae. In an embodiment, the bacterium is Escherichia Coli 83972. In some embodiments the medical device is a catheter.

In some embodiments, the present disclosure relates to a method of inhibition of pathogen colonization and growth on a silicone surface comprising attaching a plurality of ligand-derivatives to a plurality of cross-linked dendrimers; activating the silicone surface of a medical device; adsorbing the plurality of cross-linked dendrimers bound to the plurality of ligand-derivatives to the activated silicone surface; and adhering a non-pathogenic biofilm to the plurality of ligand derivatives. In an embodiment, the cross-linked dendrimers each comprise an amidation product of the amino-terminus of an amino-terminated cross-linking dendrimer. In some embodiments, the amino-terminated dendritic polymer is the G5 PAMAM. In an embodiment, the ligand-derivative, each comprises a bacterial adhesion molecule. In an embodiment of the present disclosure, the bacterial adhesion molecule is a mannose derivative. In another embodiment of the present disclosure, the bacterial adhesion molecule is PNAG. In some embodiments the non-pathogenic biofilm is highly stable. In some embodiments, the non-pathogenic biofilm provides high surface area coverage of the silicone surface. In some embodiments the non-pathogenic biofilm comprises a plurality of bacteria. In an embodiment, the bacteria comprise Escherichia Coli. In some embodiments the Escherichia. Coli lack fimbriae. In an embodiment, the bacterium is Escherichia Coli 83972. In some embodiments the silicone surface is that of a medical device. In an embodiment, the medical device is a catheter.

In some embodiments of the present disclosure the steps involved in biofilm formation generally include the initial adherence and migration of the cells on the surface, followed by aggregation and establishment of cross-linked EPS and growth of the aggregates/colonies into a mature biofilm. In some embodiments of the present disclosure the rate of biofilm formation and the density and stability of the biofilm are dependent upon the species, the host material or tissue, and the medium. For instance, it is difficult to form a stable biofilm, on a silicone surface, using wild-type E. coli 83972. The adhered bacteria cover less than 50% of the surface after 2 days in a bacterial culture, and most of the adhered bacteria can be easily detached by gentle washing with the medium. In general, bacteria with fimbriae produce biofilms faster than those without, such as wild-type E. coli 83972. However, clinical trial using fim+ E. coli 83972 mutants, expressing fimbriae, e.g. strain HU2545, to enhance biofilm formation on urinary catheters, has not been approved in the US, because of the potential virulence associated.

APPLICATIONS AND ADVANTAGES

Over 100 million urinary catheters are produced annually, which are mostly used in healthcare facilities. In the United States, around 15%-25% of hospitalized patients have to be catheterized. Over 30 million bladder catheters are used in the United States. According to the Deficit Reduction Act, hospitals will no longer receive reimbursements for CAUTI as a "reasonably preventable" health-care associated hospital infection. Antimicrobial and antiseptic-impregnated catheters have been around for a long time. However, results in multicenter randomized controlled trial and economic evaluation of these catheters show low clinical effectiveness and cost effectiveness.

The non-pathogenic biofilms disclosed herein are amenable for large scale coating process. Factory coating the catheters and other medical devices is more economical and contributes to the ease of use of these devices as compared to using a kit to coat prior to use. The biofilm composition may be used to coat a significant portion of the catheters. These catheters coated with non-pathogenic biofilms may be lyophilized for long-term storage, and are ready to use like current urinary catheters. In a smaller market, catheters or other medical devices modified with adhesion molecules may be used for in situ coating of various non-pathogenic bacteria to enhance their biofilm formation. Further, this approach is advantageous because of the flexibility in choosing the non-pathogenic bacteria to form the biofilm coatings. Due to the increasing threat of multidrug resistant infections in healthcare facility and the fact that catheter-associated urinary tract infection is the most common healthcare-acquired infection a large market for benign biofilm-coated catheters is envisioned. The method and composites of the present disclosure can also be used for surface functionalization of all other medical devices.

The method and composites can be applied to other polymer devices including indwelling catheters used for dialysis or urinary drainage (e.g., intravenous, intraperitoneal, or intravesicular), especially those made of silicone, used acutely and chronically in millions of patients every day in healthcare facilities in the US and in the global.

The non-pathogenic bacteria may include *E. coli* 83972, *E. coli* Nissle 1917, and others listed in "Darouiche R O, Hull R A. The combination of antimicrobial agents and bacterial interference to coat medical devices, EP1303256, Jan. 7, 2009.

The method and composites can be used for coating the devices with antibiofouling, antimicrobial, and/or anti-inflammatory coatings to reduce biofouling, including adsorption of proteins, adherence of bacterial and fungal cells, and inflammatory cells, including macrophages, T-lymphocytes, polymorphonuclear cells, and fibroblasts.

ADDITIONAL EMBODIMENTS

Reference will now be made to various embodiments of the present disclosure and experimental results that provide support for such embodiments. Applicants note that the disclosure herein is for illustrative purposes only and is not intended to limit the scope of the claimed subject matter in any way.

Example 1

Preparation of PAMAM-Presenting Surface on Silicone

The silicone substrates were prepared according to our publication (Lopez A I et al. Biomaterials 2011, 32, 4336-4346). Briefly, a thin layer of PDMS base and curing agent mixture was gently poured on top of a clean silicon wafer and pressed against another silicon wafer with a film of octadecyltrichlorosilane (OTS) monolayer. The OTS wafer was peeled off after curing at 110° C. overnight. The method for preparation of PAMAM-presenting surfaces on silicone substrates has also been described in detail in US20120231518, published as WO2012125576A1, and incorporated herein by reference in its entirety. Briefly for a typical example, a silicone substrate is first treated with $CO_2$ plasma for 45 seconds using a plasma generator (Harrick, PDC-32G) with low power setting (6.8 W), followed by immediate immersion in a solution of generation 5, amino-terminated poly(amidoamine) (G5 PAMAM, FIG. 1*b*) dendrimer and then washed with water. X-ray photoelectron spectroscopy (XPS) analysis of the resultant surface gave an estimated PAMAM density of $\sim 3\times 10^{12}/cm^2$, and the density of $\sim 2\times 10^{12}/cm^2$ was maintained for over 5 weeks in PBS at 37° C. (Table 1 of US20120231518).

Example 2

Preparation of Mannosylated PAMAM Dendrimers

The amounts of dry PAMAM and BiPh-Man (for preparation, see US20120231518, published as WO2012125576A1, and incorporated herein by reference in its entirety) used in the syntheses of mannosylated PAMAM dendrimers are listed in Table 2. As an example, FIG. 2*a* shows the preparation of G5-40% BiPh-Man containing on average 2-44 BiPh-Man on each PAMAM molecule. Thus, the activation of the BiPh-Man was accomplished by mixing 1-ethyl-3-(3-dimethylaminopropyl) carbodiimide hydrochloride (EDC, 10 equiv.) and N-hydroxysuccinimide (NHS, 5 equiv.) with the BiPh-Man (1 equiv.) in Millipore water for 15 min. The resultant BiPh-Man-NHS in the reaction mixture without isolation was added to the G5 PAMAM dendrimer in a vial. This mixture was stirred vigorously overnight. The resulting product was purified by gel filtration chromatography using a prepacked Sephadex PD-10 column with Millipore water as eluent, and then dried by vacuum.

TABLE 2

Amounts of dry G5 PAMAM and BiPh-Man used in the syntheses of the mannosylated PAMAM (G5-2% BiPh-Man-G5-40% BiPh-Man) and the molecular weights of the products measured by MALDI-TOF-MS.

| Mannosylated PAMAM Dendrimer[a] | G5 PAMAM | | BiPh-Man | | | MW[b] |
|---|---|---|---|---|---|---|
| | mg | µmol | mg | µmol | Equiv | (Da) |
| G5-40% BiPh-Man | 2.5 | 0.096 | 12.8 | 16 | 167 | 59435 |
| G5-32% BiPh-Man | 2.5 | 0.096 | 8.6 | 11 | 115 | 53166 |
| G5-24% BiPh-Man | 3.0 | 0.12 | 4.6 | 6.0 | 50 | 46301 |
| G5-13% BiPh-Man | 3.0 | 0.12 | 1.5 | 1.9 | 16 | 36782 |
| G5-7% BiPh-Man | 5.4 | 0.21 | 1.9 | 2.5 | 12 | 32060 |
| G5-2% BiPh-Man | 5.9 | 0.23 | 1.0 | 1.3 | 6 | 27591 |
| G5 PAMAM | — | — | — | — | — | 25962 |

[a]The degree of mannosylation and number of mannoside chains were calculated from the difference of MWs of the dendrimer before and after mannosylation, which were obtained from their MALDI-TOF mass spectra.
[b]MWs of the highest frequency fragment in the major peak from the MALDI spectra were obtained using the Voyager Data Explorer software.

All products were characterized by matrix-assisted laser desorption ionization time-of-flight (MALDI-TOF) mass spectrometry using a Voyager DE-STR MALDI-TOF mass spectrometer (Applied Biosystems), operated in the positive ion linear mode with an accelerating voltage ranging from 20 kV to 25 kV with delayed extraction. A matrix stock solution of trans-3-indoleacrylic acid (0.05 M) in a 1:1 (v/v) water/acetonitrile was first prepared. A series of dendrimer concentrations ranging from 100 to 1000 µM in Millipore water were also prepared. The analytical sample was prepared by spotting the dendrimer solution followed by the matrix solution on the MALDI plate, then dried in ambient conditions. Each mass spectrum was the average of the spectra obtained from 200 randomly located laser shots on the same sample. The MALDI spectra of the resulting mannosylated dendrimers are shown in FIG. 3 and their corresponding MWs in Table 1. Due to some defects in the PAMAM dendrimer structure, the measured MW for G5 PAMAM was 25,962 Da, which is lower than the theoretical MW of 28,828 Da. Thus, approximately 110 peripheral amino groups were assumed for the succeeding calculations instead of 128 amino groups for the ideal PAMAM. The difference in the measured MWs of mannose-modified PAMAM and the unmodified G5 provides the approximate number of BiPh-Man attached on the modified G5, and thus the degree of mannosylation.

Example 3

Preparation of Alkynylated-PAMAM (PAMAM-$A_n$)

As illustrated in FIG. 2b, where R=$CH_2$, and n~13, a solution of 4-pentynoic acid (2.2 mg, 22 µmol), N-hydroxysuccinimide (NHS, 25 mg), and 1-ethyl-3-[3-dimethylaminopropyl]carbodiimide hydrochloride (EDC, 85 mg) in water (6 mL) was stirred for 50 min. The resultant clear solution was added drop wise to a stirred solution of G5 PAMAM (5% methanol from Dendritech, Inc, took 1 mL, ~50 mg, ~1.7 µmol) in a round flask. After the addition, the first round flask was rinsed with 3 mL water and added to the second flask. The reaction mixture was stirred for 2 h at room temperature. The mixture was concentrated till about 5 mL with a rotavap under reduced pressure. To remove the low molecular weight byproducts, 1 mL of the solution was passed through a spin trap G-25 (GE Healthcare) to give PAMAM-$A_n$.

Example 4

Preparation of Azido-PNAG (PNAG-$(N_3)_m$)

Figure 2C:
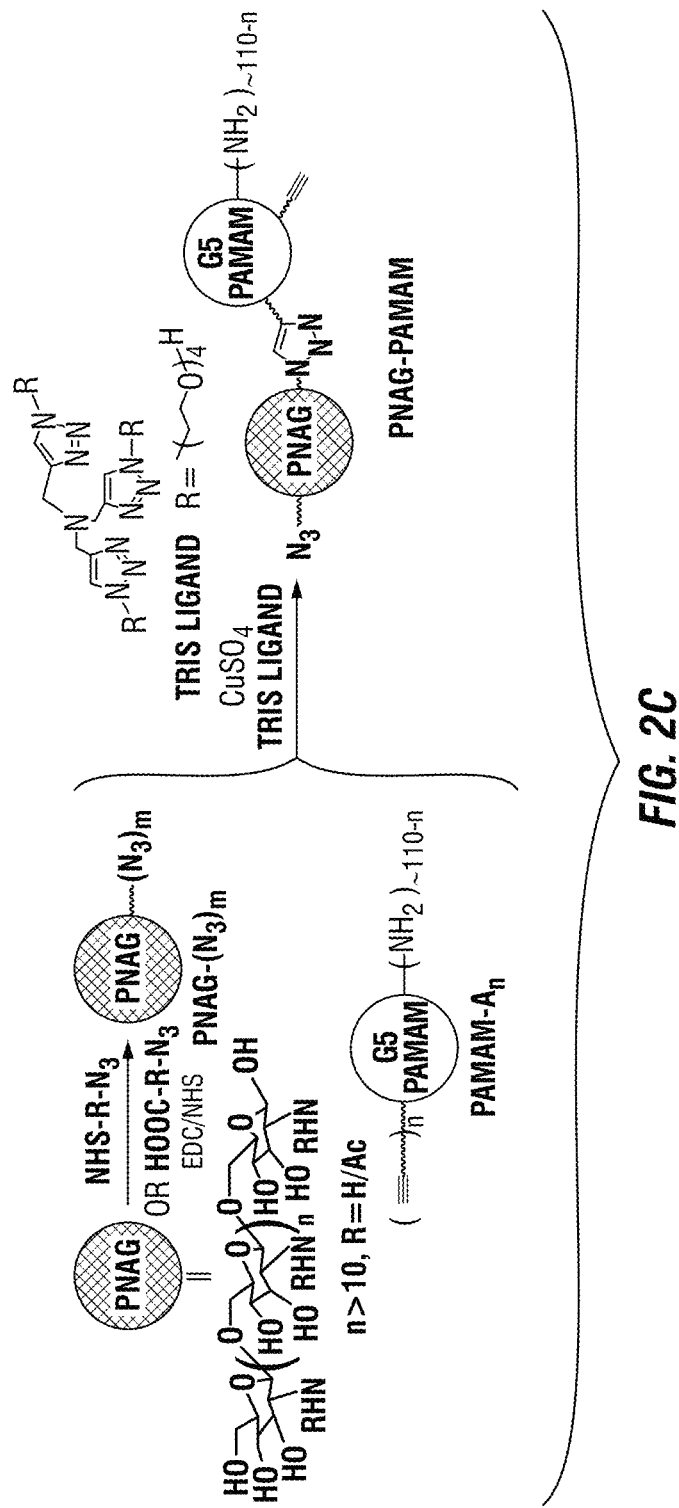

As illustrated in FIG. 2c, a solution of azidoacetic acid (0.16 mg), N-hydroxysuccinimide (NHS, 1.8 mg), and 1-ethyl-3-[3-dimethylaminopropyl]carbodiimide hydrochloride (EDC, 6 mg) in water (9 mL) was stirred for 40 min, and then PNAG (10 mg, prepared according to Goller et al. J. Bacteriology, 2006, 8022) was added. The resultant clear solution was stirred for 2 h at room temperature. The mixture was concentrated till about 1 mL with a rotavap under reduced pressure, and passed through a spin trap G-25 (GE Healthcare) to give PNAG-$(N_3)_m$.

Example 5

Preparation of PNAG-PAMAM Conjugates (PNAG-PAMAM)

As illustrated in FIG. 2C, a mixture of PNAG-$(N_3)_m$ and PAMAM-$A_n$ at a desired molar ratio in water was treated with a mixture of $CuSO_4$, tris ligand to a final concentration of 0.1 mM and 0.2 mM, respectively. To the stirred solution under $N_2$ was added sodium ascorbate to a final concentration of 2.5 mM. The mixture was stirred for 10 min at room temperature, and then quenched with sodium diethylene triamine pentaacetate (Na-DTPA, 2 mM final concentration). To remove the low molecular weight byproducts, the solution was passed through a Sephadex G-75 column and eluted with TBS buffer.

Example 6

Attaching Mannosides onto Activated Silicone and Control their Surface Presentation Two methods for preparing mannoside-presenting surfaces were developed. In the first method, G5 PAMAM dendrimer was first deposited on $CO_2$-plasma-treated silicone surfaces, followed by attaching mannosides tethering a COOH group through amidation reaction. This method has been described in detail in US20120231518, published as WO2012125576A1, and incorporated herein by reference in its entirety.

In the second method, which is more efficient, cost-effective and amendable for large scale modification of medical device, the functional molecules (for e.g. mannosides) are first attached to the amino-terminated dendritic polymers. For example, the G5 PAMAM dendrimer was first mannosylated (see FIG. 2A). By mixing of the mannoside-COOH with PAMAM at various ratios (2:1-60:1) in the presence of the activation agents (EDC/NHS), the average number (2-44) of the mannosides on the dendrimer was systematically varied, and determined by MALDI-TOF mass spectrometry. There were still a large number of free amino groups on the functionalized dendrimers, which allowed for direct covalent attachment to the plasma treated silicone surfaces. Thus, the mannosylated dendrimers (~35 µM total concentration) in water or ethanol were directly attached to the activated silicone surfaces upon incubation for 1-60 min to provide manoside-presenting surfaces (FIG. 3). No activating agent was needed. The average spacing of BiPh-Man-PAMAM (nanoclusters of BiPh-Man) could be controlled by the ratio of the modified/unmodified PAMAM dendrimers.

Alternatively, BiPh-Man can be attached to the immobilized PAMAM surfaces in the presence of activation agents EDC/NHS to provide a homogenous presentation of BiPh-Man. The density of the mannosides could be adjusted by co-deposition with oligo(ethylene glycol) end-capped with a COOH group ($EG_5$-COOH) at various ratios. Hence, Applicants can control the global versus local density of mannoside ligands on silicone surfaces. The XPS N1s signal intensity of the resultant film was similar to the one of the PAMAM film prepared by the same procedure with unmodified PAMAM. Both surface densities of PAMAM were measured to be ~$3 \times 10^{12}$ PAMAM/$cm^2$.

Example 7

Examples of the Procedure for Synthesis the Mannoside Surfaces

A 3 mM solution of BiPh-Man in Millipore water was first prepared. The carboxylic acid terminal group of the BiPh-Man was activated for 15 min using 60 mM EDC and 30 mM NHS. A 3 mM of $EG_7$NHS was prepared in cold PBS buffer and immediately used to dilute the NHS-terminated BiPh-Man to prepare following concentrations ranging from 30 µM down to 0.03 µM of the BiPhen-Man in the mixture. Activation of PDMS was performed by treatment with $CO_2$ plasma for 45 s followed by immersion in either unmodified PAMAM dendrimer solution, mannosylated G5 (G5-x % BiPh-Man-PAMAM, where x % is referred to the percentage of amino groups to be tethered with BiPh-Man) or the previously prepared solutions containing different ratios of G5-x % BiPh-Man-PAMAM/G5-PAMAM for 1 h. After 1 h, the surfaces were washed with Millipore water and dried with argon. The surfaces presenting unmodified dendrimers were then immersed in the previously prepared solutions with different ratios of NHS-activated BiPh-Man and $EG_7$-NHS for 2 h. On the other hand, the mannose surfaces obtained from the attachment of mannosylated PAMAM dendrimers (G5x % BiPh-Man-PAMAM) and the mannose surfaces presenting varied ratios of G5x % BiPh-Man-PAMAM/G5-PAMAM were immersed in a 3 mM solution of $EG_7NHS$ for 3 h to cap the remaining unreacted amino groups. Finally, all mannose surfaces were washed with Millipore water and dried with argon prior to use in bacterial assays. The XPS N1s signal intensity of the resultant film was similar to the one of the PAMAM film prepared by the same procedure with unmodified PAMAM. Both surface densities of PAMAM were measured to be ~$3 \times 10^{12}$ PAMAM/$cm^2$.

Example 8

Preparation of Alkynyl-Presenting ("Clickable") Surfaces

A stock solution of the above PAMAM-$A_n$ (n~13, 1.7 mg, ~0.5 mM based on alkynye) in 1.5 mL water and a stock solution of azido-PNAG (1.5 mg) in 1.2 mL water (~0.2 mM based on the glucosamine residues) were prepared. In this experiment, a ProPlate multi-array chamber (Grace Bio-Labs) was used to generate an array of leak-proof microwells on top of a modified silicone surface, which allows for generating various functionalized areas on the same surface.

Firstly, a PDMS substrate as a thin layer on a glass slide prepared according to the methods disclosed in Lopez A I et al. Biomaterials 2011, 32, 4336-4346, and incorporated herein by reference in its entirety, was exposed to $CO_2$ plasma for 45 s. The resulting surface oxidized PDMS was immediately attached to a ProPlate multi-array chamber which generated an array of leak-proof microwells (repeat of microwells (a)-(f), see FIG. 6) on the activated PDMS surface. 10 μl alkynyl-PAMAM (PAMAM-$A_n$) and 90 μl water were added to each of the microwells (b)-(f). The microwell array was covered, shaken for 10 min, and incubated at room temperature for 1 h.

TABLE 3

Reagents added to the microwells with a bottom of activated PDMS

| Microwell* | c | | d | | e | | f | |
|---|---|---|---|---|---|---|---|---|
| Reactant | Final conc. (mM) | Vol. (μl) | Final conc. (mM) | Vol. (μl) | Final conc. (mM) | Vol. (μl) | Final conc. (mM) | Vol. (μl) |
| PAMAM-$A_n$** | 0.025 | 10 | 0.025 | 10 | 0.025 | 10 | 0.017 | 10 |
| PNAG-$(N_3)_m$*** | 0.0125 | 12.5 | 0.025 | 25 | 0.05 | 50 | 0.17 | 250 |
| $CuSO_4$*** | 0.05 | 20 | 0.05 | 20 | 0.05 | 20 | 0.034 | 20 |
| Tris ligand*** | 0.1 | 5 | 0.1 | 5 | 0.1 | 5 | 0.069 | 5 |
| Na-ascrobate*** | 0.25 | 4 | 0.25 | 4 | 0.25 | 4 | 0.2 | 4 |
| Water total*** | | 149 | | 136 | | 111 | | — |
| Total vol. (μl) | | 200 | | 200 | | 200 | | 289 |

*Microwells (a) was only treated with water as a blank, and microwells (b) was treated with 20 μl of an alkynyl-PAMAM (PAMAM-A) as a control.

Formation of the "clickable", alkynyl presenting surfaces by adding the PAMAM-$A_n$ stock solution to the microwells on the plasma treated silicone surface.

***After forming the alkynyl-presenting surface, the microwells were washed with a flow of Millipore water, and then treated with a solution of PNAG-$(N_3)_m$, $CuSO_4$, Tris ligand, Na-ascrobate in water in the amount listed. After incubation for 10 min at room temperature, the microwells were washed with Millipore water.

Example 9

Tethering PNAG-N₃ to the Surface Via Copper-Catalyzed Click Reaction

Four experimental groups were performed for preparing the PNAG surface. For experimental group (c), the ratio of alkynyl groups on alkynyl-PAMAM and azido groups on azido-PAPGA is 2:1, and then 1:1, 1:2 and 1:10 for experimental group (d), (e) and (f), respectively. Oxidized PDMS surfaces were used as control (a), and alkylnyl-PAMAM surfaces were used as control (b).

The "click" immobilization of azido-PAPGA onto alkynyl-PAMAM surfaces was performed using $CuSO_4$, tris ligand and sodium ascorbate to generate Cu (I) catalyst in situ. Table 3 shows the concentrations of reactants for each experimental group. For each experimental group, azido-PAPGA, $CuSO_4$, tris-ligand and sodium ascorbate were first mixed in a 1.5 ml centrifuge tube according to the concentration shown in table 3 to give a clear solution. Then 200 µl of each solution was added to the corresponding experimental wells, allowing to react for 10 min. After reaction, all surfaces were rinsed with Millipore water copiously.

Example 10

Formation of Biofilms of Fim+ *E. coli* 83972 Mutant Strain HU2425

This experiment show that without surface modification of silicone elastomer, there is a very low chance of establishing a high coverage and stable non-pathogenic biofilm on the surface, even when the non-pathogenic bacteria are modified to express type 1 fimbriae, such as fim+ *E. coli* 83972 mutant strain HU2425. Further, the data show that the biofilm formation rate, density and stability by fim+ *E. coli* 83972 mutant strains HU2425 correlated to the mannoside ligands presented on the PAMAM functionalized silicone surfaces.

Example 11

Silicone Substrates with and without Mannoside Modifications

For preparation of the silicone subtracts with and without coating of PAMAM, see Sections 4.1.1. For preparation of the mannoside modified surface on silicone (Surface 3 in FIG. 4b), the PAMAM coated silicone surfaces were treated with the mannosides terminated with a COOH group (BiPh-Man, PhP-Man, TA-C3T-Man, Man, TA-C1T-Man, BiPh-F-Man, see FIG. 4) in the presence of the activating agents (EDC/NHS).

Example 12

Formation of Biofilms by Fim+ *E. coli* 83972 Mutant Strain HU2425 on the Above Modified and Unmodified Silicone Substrates The above silicone substrates were incubated with the fim+ *E. coli* 83972 suspension ($10^8$ CFU/mL) in LB (BD) containing 20 mg/mL chloramphenicol. At the end of the incubation, the substrates were rinsed with artificial urine or PBS. Some of them were shaken in the artificial urine. The densities of the adhered bacteria after 30 min and 48 hrs incubation were quantified by bright-field microscopy imaging and CFU counting (see below).

Example 13

Quantification of the Amount of Fim+*E. coli* 83972 on the Substrates

Figure 5A:
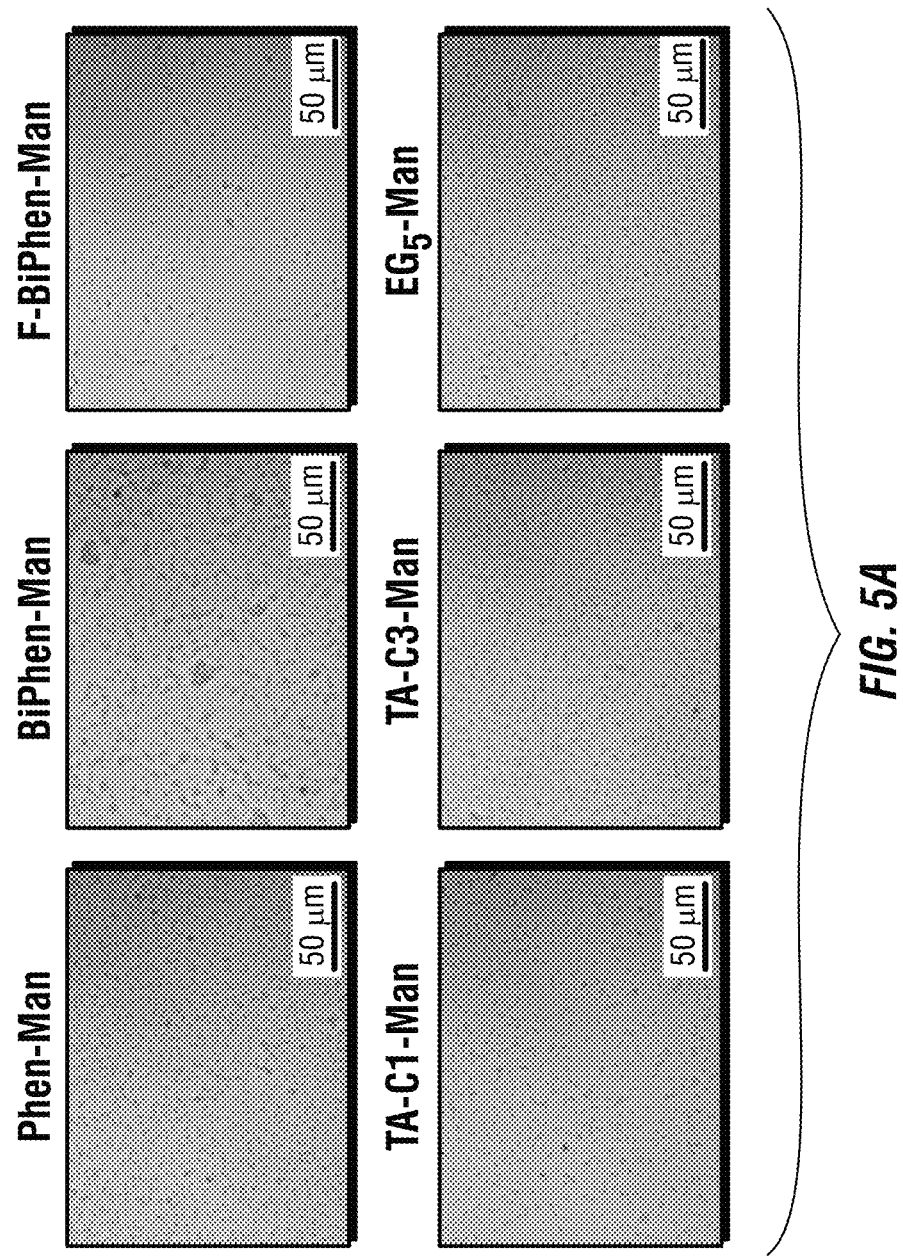
FIGS. 5A-5B depict microscopic images of fim+E. coli 83972 adhered on various mannoside surfaces after 30 min incubation in the culture of fim+E. coli 83972 (108/mL) in LB, showing that the bacterial density follows the order of BiPh-Man>PhP-Man>TA-C3T-Man~Man>TA-C1T-Man>>BiPh-F-Man~unmodified silicone (FIG. 5A-FIG. 5B).
Figure 5B:
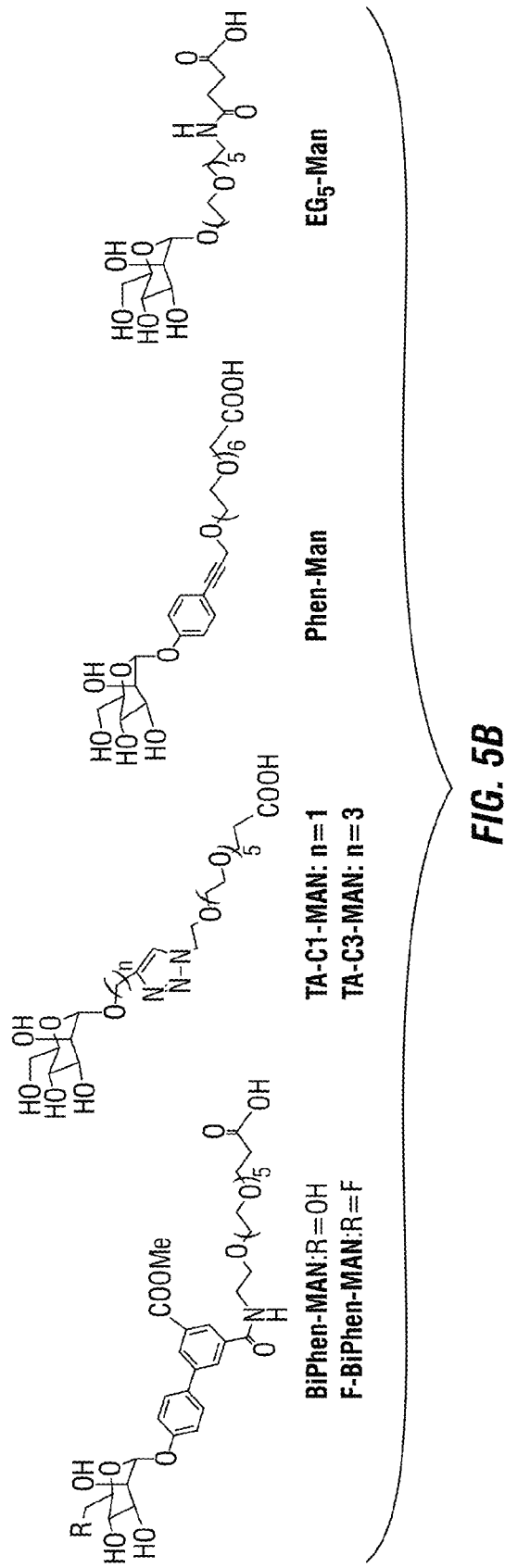

The above silicone samples were taken out from the bacterial culture, rinsed with PBS and transferred into a round bottom tubes with 1 mL artificial urine per tube, which was rinsed three times with PBS and observed with bright field microscopy imaging (FIG. 5A). Some samples were shaken in incubator shaker at 200 rpm for 10 min. At the end of shaking, the samples were taken out, rinsed by PBS and observed under microscope (for example, see FIGS. 6A-6C). At the meantime, the detached fim+*E. coli* 83972 in the AU was counted by spread on the agar. Then the samples were transferred to another 1 mL of fresh artificial urine and shook for another 10 min, followed by microscopic observation and colony counting. The total shaking time was 30 min. The bacteria remained on the surface were fully detached by 0.01% SDS with sonication and vortexing. The unmodified silicone and PAMAM surface incubated with fim+*E. coli* 83972 were treated as control. The counts of detached bacteria in AU and remained on the surface were shown in Table 4.

The result shows that the fim+ *E. coli* 83972 biofilms formed on the PhP-Man surfaces after 48 hours incubation in LB were stable against 3×10 min shaking in AU, and remained fully covering the surface (see the bottom row of FIG. 6 where alkynyl mannose is equivalent to the PhP-Man in FIG. 4) and only about 6% of fim+ *E. coli* 83972 were detached from the surface during shaking (Table 1). However, for both unmodified silicone and PAMAM surfaces, more than half of the fim+ *E. coli* 83972 were detached and did not cover the surfaces. The amount of remaining fim+ *E. coli* 83972 on the PhP-Man surfaces was 192 times more than on the unmodified silicone substrates.

TABLE 4

Counting of detached fim+ *E. coli* 83972 in AU and remained fim+ *E. coli* 83972 on PDMS, PAMAM and PhP-Man surfaces.

| Surfaces | Detached bacterial in AU ($10^4$ CFU/mL) | | | Bacterial Remained on the surface ($10^4$ CFU/cm²) | Ratio of remained bacterial (%) |
| --- | --- | --- | --- | --- | --- |
| | 10 min | 2 × 10 min | 3 × 10 min | | |
| PDMS | 10.3 ± 3.3 | 2.6 ± 0.7 | 1.9 ± 0.6 | 13.3 ± 5.8 | 47.3 |
| PAMAM | 56.0 ± 12.4 | 12.2 ± 4.5 | 11.3 ± 3.6 | 70.8 ± 7.6 | 47.1 |
| Alkynyl mannose | 89.7 ± 16.4 | 50.8 ± 8.2 | 18.7 ± 5.3 | 2583.3 ± 622.6 | 94.2 |

Example 14

Figures 1, 7A:
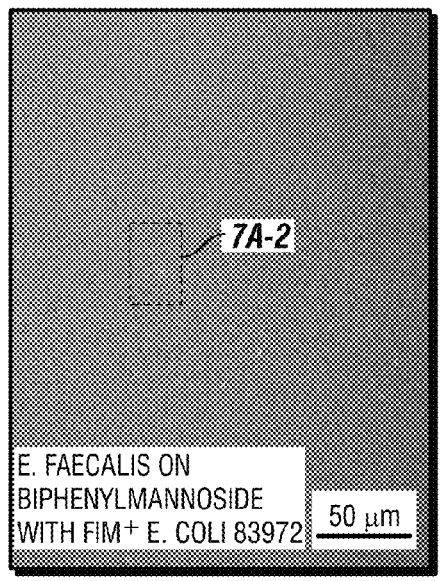
FIGS. 7A-7C show an overlay of reflected brightfield and green fluorescence images of a pre-formed biofilm of fim+E. coli 83972 on BiPh-Man surface after 11 days of incubation in $10^8$ CFU/mL of E. faecalis in LB, showing that the surface remained fully covered by fim+E. coli 83972 biofilm (FIG. 7A-1) with few E. faecalis fluorescing green (see the magnified image FIG. 7A-2).
Figures 2, 7A:
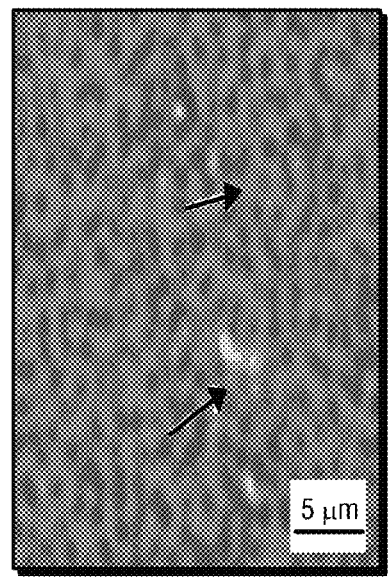

Comparison of E. coli 83972 Mutant Strain HU2425 Coatings on Various Modified and Unmodified Silicone Surfaces Against Pathogen Colonization To test performance of various coatings of *E. coli* 83972 mutant strain HU2425 against pathogenic colonization, we initially challenged the coatings with a strong biofilm-forming *E. faecalis* strain in lysogeny broth (LB), a nutrition rich medium. The benign biofilms were incubated with the challenge bacteria suspension ($10^8$ CFU/mL, replaced every day with a newly prepared culture) in LB for 11 days. Notably, this pathogen concentration was 3 orders of magnitudes higher than the diagnostic threshold of UTI. Remarkably, *E. coli* 83972 mutant strain HU2425 biofilms on BiPh-Man and PhP-Man surfaces remained nearly intact after 11 days (FIG. 7a). In contrast, all other mannoside surfaces and unmodified silicone surfaces had been colonized by *E. faecalis* and substantial portions of fim+ *E. coli* 83972 detached from the surfaces. The performance of the fim+ *E. coli* 83972 biofilm on the surfaces presenting the mannosides (see FIG. 4) follows the order of BiPh-Man>PhP-Man>TA-C3T-Man>Man>TA-C1T-Man>>BiPh-F-Man≈unmodified silicone (FIG. 3b). See US20120231518, published as WO2012125576A1, and incorporated herein by reference in its entirety for details.

Example 15

Figure 7B:
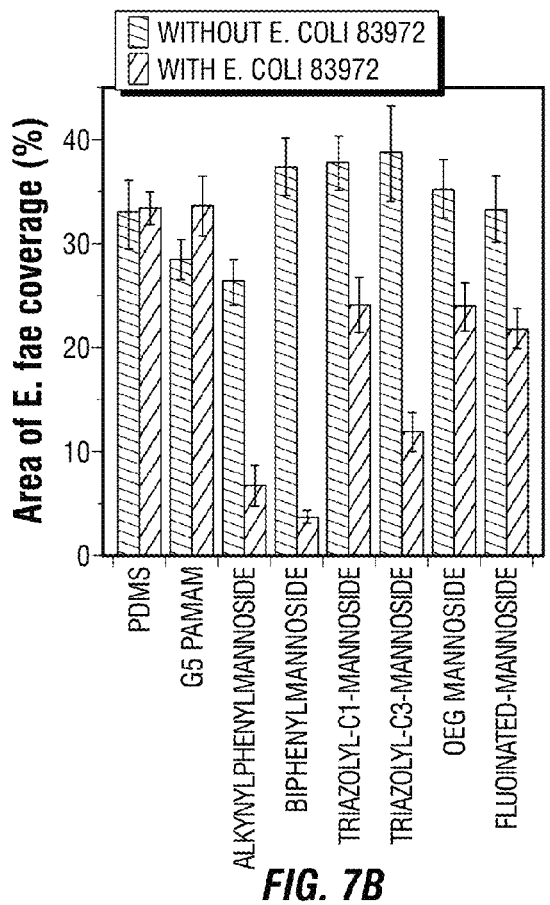
Figure 7C:
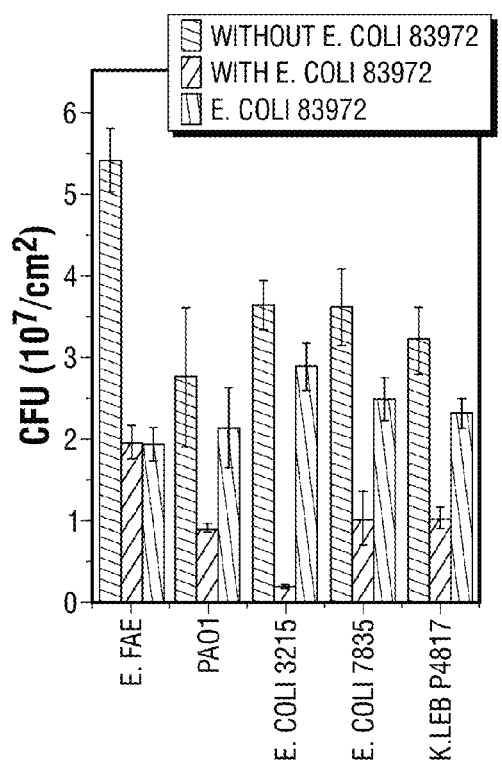

Quantification of the Amount of Pathogens and Fim+ E. coli 83972 on the Substrates Fluorescence microscopy imaging was initially used to visualize and quantify a low density of fluorescently labeled pathogen on the biofilm (for an example, see FIGS. 7A-7B for details). For general quantification of all other bacteria, we used conventional plating method for counting the colony forming units (CFU) of the pathogens and *E. coli* 83972. We verified that bacterial biofilms could be completely detached by sonication for 10 min in 0.01% sodium dodecyl sulfate (SDS), and the bacteria remained viable. Differential quantification of the pathogens and *E. coli* 83972 is based on selective culture in LB agar with the amount of antibiotics list in Table 5, which prevents the growth of *E. coli* 83972 without influencing the growth of the pathogen over a wide concentration range ($10^2$-$10^8$ CFU/mL) and the ratio of the two bacteria (1:$10^5$). Likewise, *E. coli* 83972 was quantified by selective culture with 20 mg/mL chloramphenicol to remove the pathogens. For single-sided substrates, errors due to bacteria adhered on the uncoated backside of the substrate (usually <$2\times10^3$ CFU/cm$^2$) were corrected using an uncoated substrate as control.

TABLE 5

| | Pathogens and antibodies for selective culture | | | | |
|---|---|---|---|---|---|
| Uropathogen | PAO1 | E. faecalis OG1RF | Klebsiella 4817 | E. coli 7835 | E. coli 3215 |
| Antibotics for selective culture | Tetracycline 4 µg/mL | Tetracycline 4 µg/mL | Carbenicillin 100 µg/mL | Ampicillin 100 µg/mL | Ampicillin 100 µg/mL |

Example 16

Challenge by (Mixtures) of Drug-Resistant Uropathogens

After identifying that fim+ *E. coli* 83972 biofilms on the BiPh-Man and PhP-Man surfaces performed the best, we then challenged these biofilms with 5 clinical uropathogenic isolates (Table 5) for 10 days. To mimic the in vivo conditions, the biofilms formed on BiPh-Man surfaces were challenged with mixtures of uropathogens listed in Table 2 in artificial urine, prepared according to Brooks et al. (*Letters in Applied Microbiology* 1997, 24, 203-206) at 37° C. for 11 days. Each day, the culture was replaced with freshly prepared bacterial suspension ($10^5$ CFU/mL) of each pathogen. Untreated PDMS surfaces with and without fim+ *E. coli* 83972 biofilms prepared identically as those on BiPh-Man surfaces were used as the controls. At the end of the bacterial interference, the surfaces were rinsed 3 times with PBS, shook twice in 1 mL AU at 200 rpm for 20 min. Using selective culture and plating, the fim+ *E. coli* 83972 and combined pathogens remained on the surface are quantified. The results are listed in Table 6, showing that fim+ *E. coli* 83972 on unmodified silicone surfaces could not outcompete with the uropathogens, while all pathogens could not be detected (<100/cm$^2$) on the fim+ *E. coli* 83972 biofilms formed on the BiPh-Man surfaces and the protective biofilms remained fully covering the surface.

TABLE 6

Amounts (CFU/cm$^2$) of the remained pathogens and fim+ E. coli 83972 (in parentheses) on the PDMS surfaces with/without biphenyl mannosides modification and with/without fim+ E. coli 83972 biofilms after continuously challenging with mixtures of uropathogens (10$^5$ CFU/mL each) for 11 days in artificial urine.

| Challenging bacteria | E. coli 3215 + E. coli 7835 | E. coli 3215 + Klebsiella 4817 | E. coli 7835 + Klebsiella 4817 | E. coli 3215 + E. coli 7835 + Klebsiella 4817 |
|---|---|---|---|---|
| Unmodified PDMS | 49 ± 6 × 10$^2$ | 68 ± 5 × 10$^2$ | 58 ± 9 × 10$^2$ | 73 ± 4 × 10$^2$ |
| fim+ E. coli 83972 on unmodified PDMS | 45 ± 4 × 10$^2$ (7 ± 0.5 × 10$^2$) | 51 ± 6 × 10$^2$ (5 ± 0.8 × 10$^2$) | 49 ± 2 × 10$^2$ (9 ± 0.6 × 10$^2$) | 60 ± 2 × 10$^2$ (10 ± 1 × 10$^2$) |
| fim+ E. coli 83972 on BiPh-Man-PDMS | <100 (38 ± 4 × 10$^4$) | <100 (31 ± 4 × 10$^4$) | <100 (35 ± 6 × 10$^4$) | <100 (36 ± 4 × 10$^4$) |

With some modifications to the above protocol, the following provide another example demonstrating that a stable and high coverage fim+ E. coli 83972 biofilm is needed to protect the surface against pathogenic colonization. After 2 days static incubation at 37° C., the PhP-Man modified surface with fim+ E. coli 83972 biofilms (Experimental group) were transferred into the uropathogen culture (10$^5$ CFU/mL for each strain) in artificial urine (AU) prepared according to the literature (*Letters in Applied Microbiology* 1997, 24, 203-206). PhP-Man modified surfaces without fim+ E. coli 83972 (Control group I), unmodified silicone surfaces without fim+ E. coli 83972 (Control group II), unmodified silicone (Control group III) and PAMAM modified silicone (Control group IV) after subjected to the same condition for formation of fim+ E. coli 83972 biofilms on the mannoside surfaces were treated as the control groups. All the samples were changed with fresh AU culture every day for up to 3 days or 11 days at 37° C. At the end of the bacterial interference experiment, the surface was rinsed with PBS and transferred to 1 mL 0.01% sodium dodecyl sulfate (SDS), sonicated for 20 min followed by vortexing for additional 1.5 min. Detached bacteria were diluted and spread on the agar with appropriate antibiotics. The bacterial colonies formed after 24 h incubation at 37° C. The data represented the mean of at least 3 experiments (Table 7).

TABLE 7

Performance of bacterial interference of fim+ E. coli 83972 against single or multiple strains of pathogenic E. faecalis, E. coli 3215 and E. coli 7835 for 3 days (10$^4$ CFU/cm$^2$) and 11 days (10$^6$ CFU/cm$^2$).

| | Control I | Control II | Control III | Control IV | Experimental |
|---|---|---|---|---|---|
| After 3 days | | | | | |
| fim+ E. coli 83972 | — | — | 1.2 ± 0.1 | 2.6 ± 0.9 | 1750.0 ± 234.9 |
| E. faecalis | 7.5 ± 1.1 | 5.6 ± 1.1 | 1.3 ± 0.4 | 0.7 ± 0.1 | <0.01 |
| fim+ E. coli 83972 | — | — | 1.9 ± 0.4 | 3.6 ± 0.7 | 2133.3 ± 391.3 |
| E. coli 3215 | 11.8 ± 1.6 | 8.8 ± 1.0 | 3.0 ± 0.7 | 2.0 ± 0.2 | <0.01 |
| fim+ E. coli 83972 | — | — | 2.2 ± 0.4 | 3.3 ± 0.7 | 2816.7 ± 628.4 |
| E. coli 7835 | 13.0 ± 3.2 | 8.3 ± 1.1 | 2.8 ± 0.6 | 1.8 ± 0.4 | <0.01 |
| fim+ E. coli 83972 | — | — | 1.8 ± 0.5 | 3.1 ± 0.8 | 1666.7 ± 304.0 |
| E. faecalis + E. coli 7835 | 12.0 ± 2.3 | 7.2 ± 1.7 | 2.7 ± 0.8 | 1.7 ± 0.5 | <0.01 |
| After 11 days | | | | | |
| fim+ E. coli 83972 | — | — | 0.008 ± 0.0007 | 0.007 ± 0.001 | 7.1 ± 2.2 |
| E. faecalis | 21.5 ± 5.4 | 15.7 ± 2.1 | 19.3 ± 4.6 | 28.3 ± 4.1 | 0.05 ± 0.009 |
| fim+ E. coli 83972 | — | — | 0.003 ± 0.0004 | 0.004 ± 0.0007 | 9.0 ± 1.7 |
| E. coli 3215 | 32.0 ± 4.6 | 24.3 ± 2.7 | 26.3 ± 3.7 | 38.2 ± 7.8 | 0.09 ± 0.002 |
| fim+ E. coli 83972 | — | — | 0.004 ± 0.0005 | 0.003 ± 0.0005 | 8.7 ± 1.7 |
| E. coli 7835 | 36.0 ± 3.5 | 25.7 ± 5.2 | 30.7 ± 8.4 | 30.3 ± 8.5 | 0.02 ± 0.005 |
| fim+ E. coli 83972 | — | — | 0.001 ± 0.0002 | 0.0001 ± 0.0002 | 4.5 ± 0.6 |
| E. faecalis + E. coli 7835 | 21.3 ± 1.4 | 23.7 ± 6.7 | 37.3 ± 5.1 | 38.5 ± 6.6 | 0.02 ± 0.008 |

After 3 days interference, fim+ E. coli 83972 presented on the alkynyl mannose surface kept similar adherence for all challenge groups (1.7, 2.1, 2.8, 1.7×10$^6$ CFU/cm$^2$). The fim+ E. coli 83972 biofilm protected the surface against the uropathogenic colonization; the challenging uropathogens could be barely detected, compared to the unmodified silicone surface (<100 CFU/cm$^2$ vs. 7.5, 11.8, 13.0, 12.0×10$^4$ CFU/cm$^2$). Multiple strains of uropathogens were also efficiently shielded by the fim+ E. coli 83972 biofilms. However, the control group III and IV, which were silicone and PAMAM-coated silicone surfaces pretreated with fim+ E. coli 83972 for 2 days showed low coverage of fim+ E. coli 83972 and limited capability of shielding the pathogens. Coating of the benign biofilms significantly decreased the colonization of the pathogens by 100 times.

The fim+ E. coli 83972 biofilms on the alkynyl mannose surfaces still inhibited the colonization of the pathogens by 100 times than on the unmodified silicone surface in AU after 11 days under constant challenging by high concentration of uropathogens. The result indicated that the coverage and stability of the fim+ E. coli 83972 biofilms were crucial for preventing the pathogens adhesion.

Example 17

Figure 8A:
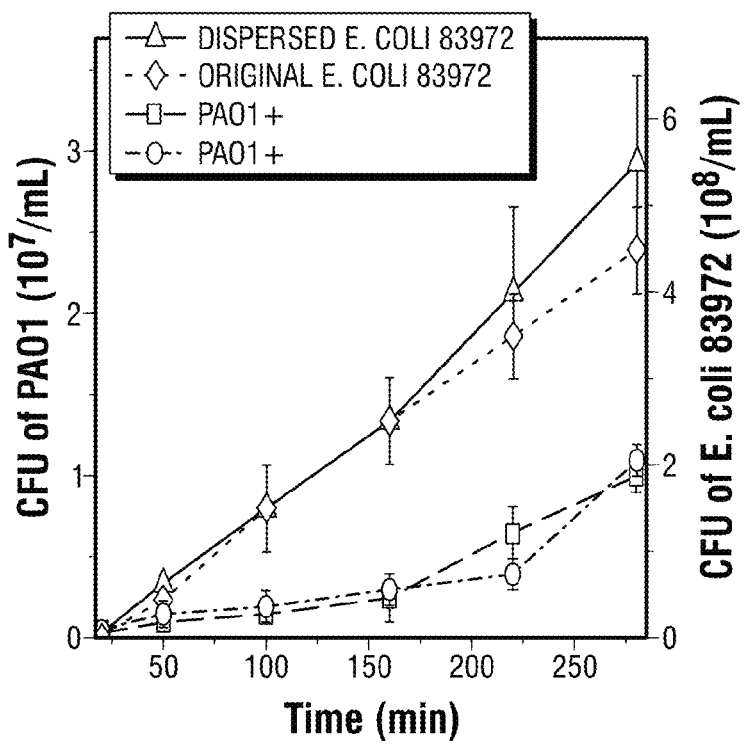
FIGS. 8A-8B show a comparison of dispersed vs. original fim+ E. coli 83972 for interference with PAO1 (FIG. 8A) and E. coli 3215 (FIG. 8B) in artificial urine.
Figure 8B:
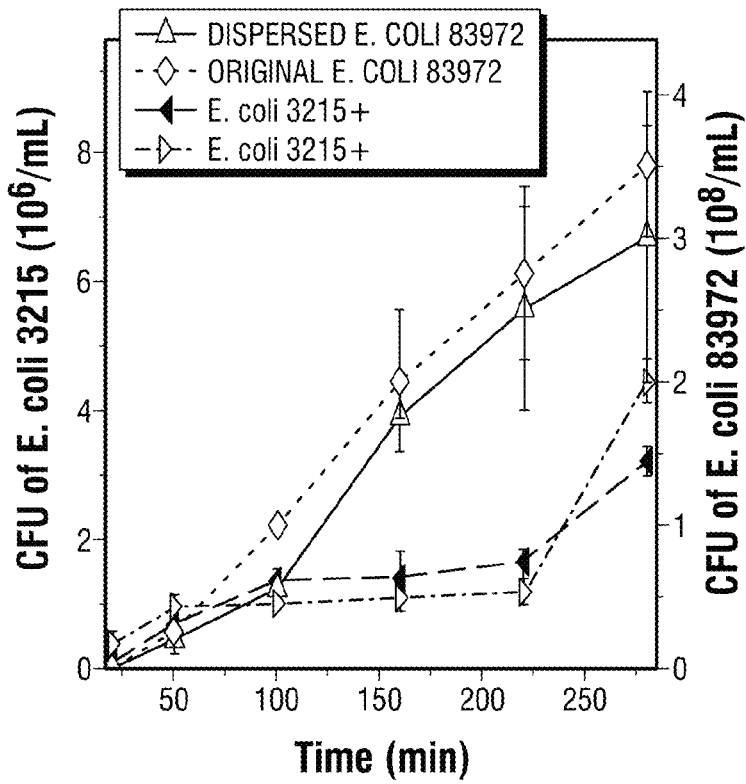
Figure 10A:
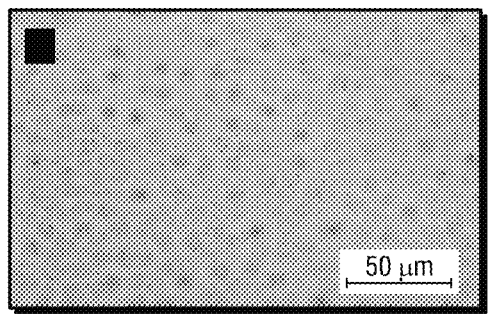
FIGS. 10A-10F show wild-type E. coli 83972 biofilms formed on microwells defined with a ProPlate multi-array chamber (illustrated on the top) on a $CO_2$ plasma treated silicone surface (FIG. 10A), and silicone surfaces presenting alkynyl-PAMAM (FIG. 10B), alkynyl-PAMAM/PNAG-N3 2:1 (FIG. 10C), alkynyl-PAMAM/PNAG-N3 1:1 (FIG. 10D), alkynyl-PAMAM/PNAG-N3 1:2 (FIG. 10E), and alkynyl-PAMAM/PNAG-N3 1:10 (FIG. 10F).
Figure 10B:
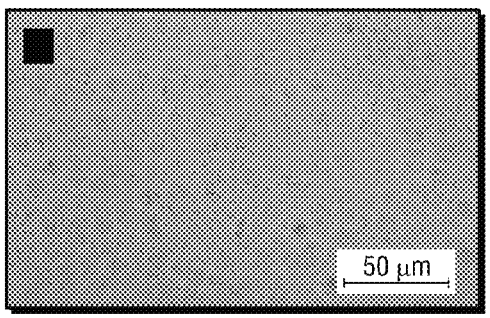
Figure 10C:
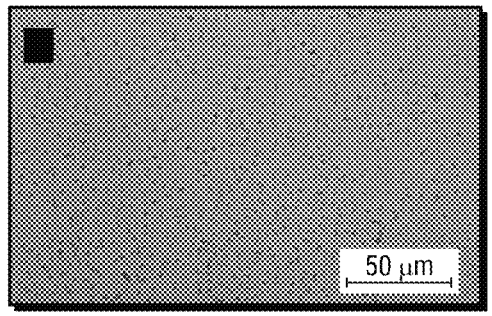
Figure 10D:
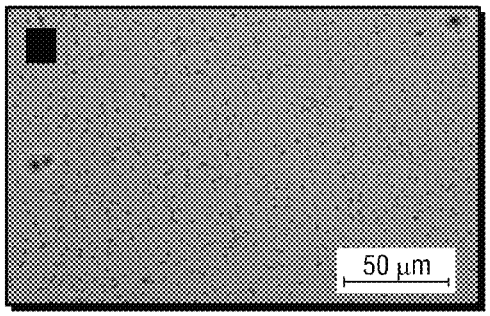
Figure 10E:
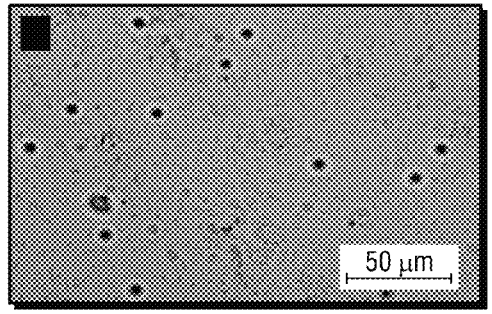
Figure 10F:
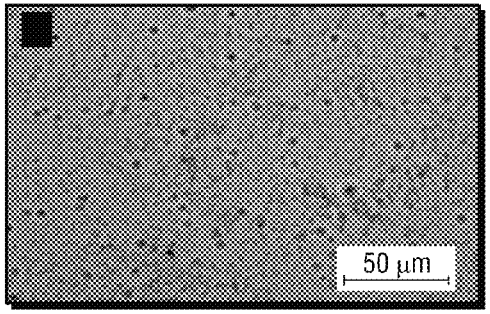

Interfering the Growth of Pathogens in Artificial Urine by Fim+ E. coli 83972 Dispersed from Biofilms This experiment proves that fim+ E. coli 83972 biofilm can continuously deploy bacteria to outcompete the uropathogens for growth in urine. Thus, a fim+ E. coli 83972 biofilm grown on PhP-Man surface was washed 3 times in PBS to remove the physiosorbed bacteria, and then incubated in LB for 24 h at 37° C. The dispersed bacteria were grown to OD$_{600}$ 0.5. Artificial urine was prepared according to (Letters in Applied Microbiology 1997, 24, 203-206), and was used to adjust the OD$_{600}$ of dispersed fim+ E. coli 83972, original fim+ E. coli 83972, two uropathogens—pseudomonas aeruginosa (PAO1) and E. coli 3215– to 0.05. Each pathogen and dispersed fim+ E. coli 83972 was mixed 1:1 to a total volume of 10 mL with OD$_{600}$ of 0.05, and pathogen mixed with original fim+ E. coli 83972 was the control. The suspensions were incubated at 37° C. and 200 rpm. FIG. 8 shows that the dispersed fim+ E. coli 83972 performed equally well compared with the original strain in outcompeting the growth of PAO1 and the uropathogenic isolate E. coli 3215.

Example 18

Biofilm Formation of Wild-Type E. coli 83972 on the PNAG Surfaces

Wild-type E. coli 83972 was grown in 10 ml of Luria Bertani (LB) (BD, Franklin Lakes, N.J.) media containing 20 µg/ml chloramphenicol (Sigma Aldrich, St. Louis, Mo.). After overnight incubation, the optical density at 600 nm (OD$_{600}$) was adjusted to 0.25, corresponding to a bacterial concentration of 10$^8$ CFU/ml.

All surfaces in the ProPlate chamber were inoculated with the above LB media (200 µL/well) containing wild-type E. coli 83972 with a bacterial concentration of 10$^8$ CFU/ml. Then the surfaces were incubated for 24 h at 37° C. After the incubation, the surfaces were rinsed three times with PBS prior to remove the silicone gasket and upper structure from the glass slide. Then all surfaces were rinsed with Millipore water copiously. All surfaces were then imaged under the reflected brightfield using a Nikon 80i microscope (Nikon Instruments, Melville, N.Y.) with a 40× objective and a CoolSnap HQ2 camera (Photometrics, Tucson, Ariz.). Selected images are presented in FIG. 10.

From the foregoing description, one skilled in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

REFERENCES 1. (http://en.wikipedia.org/wiki/Biofilm).

What is claimed is:

1. A method of making a modified silicone surface comprising:
    activating the silicone surface;
    mixing a plurality of cross-linking dendrimers with a plurality of ligand derivatives to allow binding of dendrimers to ligand derivatives, wherein the plurality of cross-linking dendrimers comprise an alkynylated generation 5 poly(amido amine) dendrimer and the plurality of ligand derivatives comprise azido-poly-N-acetyl-glucosamine; and
    functionalizing the silicone surface by immobilizing the plurality of the cross-linked dendrimers bound to the plurality of ligand derivatives on the activated silicone surface; and
    adhering a non-pathogenic biolfilm to the modified silicone surface, wherein the functionalizing provides a ligand-presenting modified silicone surface conducive for the formation and accumulation of a non-pathogenic biofilm.

2. The method of claim 1, wherein the modified silicone surface interferes with pathogen colonization.

3. The method of claim 1, wherein the activating comprises oxidizing of the silicone surface.

4. The method of claim 3, wherein the oxidizing comprises treatment with CO$_2$ plasma.

5. The method of claim 4, wherein the treatment with CO$_2$ plasma is for about 30 s to about 60 s.

6. The method of claim 4, wherein the treatment with CO$_2$ plasma is at a low power setting.

7. The method of claim 6, wherein the power setting ranges from about 1 W to about 10 W.

8. The method of claim 1, wherein the activated silicone surface comprises poly(dimethylsiloxane).

9. The method of claim 1, wherein the plurality of ligand derivatives are mixed with an activating agent prior to mixing with the plurality of the cross-linking derivatives.

10. The method of claim 9, wherein the activating agent comprises 1-ethyl-3-(3-dimethylaminopropyl) carbodiimide hydrochloride and N-hydroxysuccinimide.

11. The method of claim 1, wherein the mixing of the plurality of ligand derivatives with the plurality of cross-linked dendrimers is in the ratio ranging from about 2:1 to about 60:1.

12. The method of claim 1, wherein the non-pathogenic biofilm comprises a plurality of bacteria.

13. The method of claim 12, wherein the bacteria comprise E. coli 83972.

14. The method of claim 12, wherein the bacteria comprise fim+E. coli mutant strain HU2425.

15. A method of making a modified silicone surface comprising:
    activating the silicone surface;
    immobilizing a plurality of cross-linking dendrimers on the activated silicone surface; and binding a plurality of ligand derivatives to the immobilized plurality of cross-linking dendrimers in the presence of an activating agent, wherein the the plurality of ligand derivatives comprise a bacterial adhesion molecule;

co-depositing oligo(ethylene)glycol linker, wherein the oligo(ethylene)glycol linker is end-capped with a carboxyl group, and wherein the co-deposition of the oligo(ethylene)glycol linker controls the density of the ligand-derivatives on the modified silicone surface; and adhering a non-pathogenic biofilm to the modified silicone surface.

16. The method of claim 15, wherein the modified silicone surface interferes with pathogen colonization.

17. The method of claim 15, wherein the plurality of cross-linking dendrimer comprise a dendrimeric moiety selected from the group consisting of poly (amido amine) polylysine, poly(amino acid), polyallylamine, polyamines, poly(proplyl imine), and combinations thereof.

18. The method of claim 15, wherein the plurality of cross-linking dendrimers comprise a generation 5 poly (amido amine) dendrimer.

19. The method of claim 15, wherein the plurality of ligand derivatives comprise mannose derivatives.

20. The method of claim 19, wherein the mannose derivatives are selected from BiPh-Man, PhP-Man, TA-C3T-Man, Man, TACIT-Man, BiPh-F-Man.

21. The method of claim 15, wherein the plurality of ligand derivatives comprise poly-3-(1-6)-N-acetyl-D-glucosamine (PNAG).

22. A modified silicone surface comprising:
a plurality of the cross-linked dendrimers bound to a plurality of ligand derivatives immobilized on the silicone surface to form a functionalized ligand-presenting silicone surface, wherein the plurality of ligand derivatives comprise a bacterial adhesion molecule; and
a non-pathogenic biolfilm adhered to the functionalized ligand-presenting silicone surface, wherein the modified silicone surface interferes with pathogen colonization.

23. The modified silicone surface of claim 22, wherein the plurality of cross-linked dendrimers bound to the plurality of ligand derivatives are immobilized on the silicone surface via activation of the silicone surface.

24. The modified silicone surface of claim 23, wherein the activation of the silicone surface comprises oxidizing of the silicone surface.

25. The modified silicone surface of claim 22, wherein the modified silicone surface comprises poly(dimethylsiloxane).

26. The modified silicone surface of claim 22, wherein the plurality of the cross-linked dendrimers are bound to the plurality of ligand derivatives in presence of an activating agent.

27. The modified silicone surface of claim 22, the plurality of cross-linking dendrimers comprise a generation 5 poly(amido amine) dendrimer.

28. The modified silicone surface of claim 22, wherein the plurality of ligand derivatives comprise mannose derivatives.

29. The modified silicone surface of claim 28, wherein the mannose derivatives are selected from BiPh-Man, PhP-Man, TA-C3T-Man, Man, TACIT-Man, BiPh-F-Man.

30. The method of claim 22, wherein the plurality of ligand derivatives comprise poly-β-(1-6)-N-acetyl-D-glucosamine (PNAG).

31. The modified silicone surface of claim 22, wherein the ratio of the plurality of ligand derivatives to the plurality of cross-linked dendrimers ranges from about 2:1 to about 60:1.

32. The modified silicone surface of claim 22, wherein the non-pathogenic biofilm comprises a plurality of bacteria.

33. The modified silicone surface of claim 32, wherein the bacteria comprise *E. coli* 83972.

34. The modified silicone surface of claim 32, wherein the bacteria comprise fim+*E. coli* mutant strain HU2425.

35. The modified silicone surface of claim 22, wherein the surface is that of an implantable medical device.

36. A medical device comprising a modified silicone surface, the modified silicone surface comprising:
an activated silicone layer;
a plurality of activated dendrimers absorbed on to the activated silicone layer;
a plurality of ligand derivatives, each bound to at least one of the plurality of cross-linked dendrimers, wherein the plurality of ligand derivatives comprise a bacterial adhesion molecule; and
a non-pathogenic biofilm adhered to the plurality of ligand derivatives.

37. The medical device of claim 36, wherein the modified silicone surface contributes to the inhibition of pathogen colonization and growth.

38. The medical device of claim 36, wherein the cross-linked dendrimers each comprise an amidation product of the amino-terminus of an amino-terminated cross-linking dendrimer.

39. The medical device of claim 38, wherein the amino-terminated dendritic polymer is the G5 PAMAM.

40. The medical device of claim 36, wherein the bacterial adhesion molecule is a mannose derivative.

41. The medical device of claim 36, wherein the bacterial adhesion molecule is PNAG.

42. The medical device of claim 36, wherein the non-pathogenic biofilm comprises a plurality of bacteria.

43. The medical device of claim 42, the bacteria comprise *Escherichia Coli*.

44. The medical device of claim 43, wherein the *Escherichia Coli* lack fimbriae.

45. The medical device of claim 43, wherein the bacteria is *Escherichia Coli* 83972.

46. A modified silicone surface comprising:
a plurality of the cross-linked dendrimers bound to a plurality of ligand derivatives immobilized on the silicone surface to form a functionalized ligand-presenting silicone surface, wherein the plurality of cross-linking dendrimers comprise an alkynylated generation 5 poly (amido amine) dendrimer and the plurality of ligand derivatives comprise azido-poly-N-acetyl-glucosamine; and
a non-pathogenic biofilm adhered to the functionalized ligand-presenting silicone surface, wherein the modified silicone surface interferes with pathogen colonization.

47. A method of making a modified silicone surface comprising:
activating the silicone surface;
mixing a plurality of cross-linking dendrimers with a plurality of ligand derivatives to allow binding of dendrimers to ligand derivatives, wherein the plurality of ligand derivatives comprise a bacterial adhesion molecule; and
functionalizing the silicone surface by immobilizing the plurality of the cross-linked dendrimers bound to the plurality of ligand derivatives on the activated silicone surface; and
adhering a non-pathogenic biolfilm to the modified silicone surface, wherein the functionalizing provides a ligand-presenting modified silicone surface conducive for the formation and accumulation of a non-pathogenic biofilm.

* * * * *